(12) United States Patent
Stocker et al.

(10) Patent No.: US 6,617,450 B1
(45) Date of Patent: Sep. 9, 2003

(54) P-GLYCOPROTEINS AND USES THEREOF

(75) Inventors: Penny J. Stocker, Jamaica Plain, MA (US); Dorothy T. Steimel-Crespi, Marblehead, MA (US); Charles L. Crespi, Marblehead, MA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/672,810

(22) Filed: Sep. 28, 2000

Related U.S. Application Data

(60) Provisional application No. 60/158,818, filed on Oct. 12, 1999, and provisional application No. 60/156,921, filed on Sep. 28, 1999.

(51) Int. Cl.$^7$ .......... C07H 21/04; C07K 1/00; C07K 14/00; C07K 17/00; C12N 1/20; C12N 15/00; C12N 15/09; C12N 15/63; C12N 15/70; C12N 15/74

(52) U.S. Cl. .......... 536/235; 530/350; 530/388.9; 435/252.3; 435/320.1

(58) Field of Search ............ 530/350, 388.9; 536/23.5; 435/252.3, 320.1

(56) References Cited

U.S. PATENT DOCUMENTS 5,429,921 A  7/1995  Harpold et al.

FOREIGN PATENT DOCUMENTS

| WO | WO 87/05943 A | 10/1987 |
| WO | WO 93/02105 A | 2/1993 |
| WO | WO 98/13072 A | 4/1998 |

OTHER PUBLICATIONS

GenBank accession No. AF045016, Puel et al., Feb. 7, 1998.
GenBank accession No. AF092810, Steingold et al. Oct. 4, 1998.
Genbank accession No. M14758, Chen et al., Dec. 13, 1999.
Genbank accession Nos. AF016535 of NM$_{13}$000927, Chen et al. Sep. 3, 1997.
Sharom et al., *Biochem. Pharmacol.* 58:571–586, 1999.
Sugden et al., *Mol. Cell Biol.* 5:410–413, 1985.
Yates et al., *Nature (Lond.)* 313: 812–815, 1985.
Sarkadi et al., *J. Biol. Chem.* 267: 4854–4858, 1992.
Druekes et al., *Anal. Biochem.* 230: 173–177, 1995.
U.S. patent application No. 09/672,725; Stocker et al., filed Sep. 28, 2000.
Steingold et al., *Anticancer Res.* 18: 393–400 (1998).
Capella et al., *Zeitschrift Naturforsch.* 54c: 119–127 (1999).
Schrenk et al., *Hepatology* 17:854–860 (1993).
Motomura et al., *Blood* 91(9): 3163–3171 (1998).
Romagnoli et al., *Biol. Chem.* 380: 553–559 (1999).
Fox et al., *Drug Metab. Revs.* 32(Supp 1): p. 41 (2000).

Primary Examiner—Rebecca E. Prouty
Assistant Examiner—Manjunath N. Rao
(74) Attorney, Agent, or Firm—Wolf, Greenfield & Sacks, PC

(57) ABSTRACT

The invention pertains to cynomologous monkey P-glycoproteins and related P-glycoproteins which include cynomologous-specific amino acids, as well as nucleic acids which encode those polypeptides. The present invention also includes fragments and biologically functional variants of the cynomologous monkey P-glycoprotein. The invention further relates to methods of using such cynomologous monkey P-glycoprotein nucleic acids and polypeptides, especially in methods for determining bioavailability of drugs and for screening for inhibitors of cynomologous PGP. Also included are cynomologous PGP inhibitors which inhibit cynomologous PGP activity by inhibiting the expression or function of cynomologous PGP.

18 Claims, No Drawings

P-GLYCOPROTEINS AND USES THEREOF

RELATED APPLICATIONS

This application claims priority under 35 U.S.C. §119 to U.S. provisional application serial No. 60/158,818, filed Oct. 12, 1999, and to U.S. provisional application serial No. 60/156,921, filed Sep. 28, 1999.

FIELD OF THE INVENTION

The invention pertains to P-glycoproteins of cynomologous monkey (*Macaca fascicularis*).

BACKGROUND OF THE INVENTION

P-glycoprotein (PGP; also known as multidrug transporter, MDR1) is a member of the ABC transporter superfamily and is expressed in the human intestine, liver and other tissues. This enzyme serves as an efflux pump exporting small molecules across the cell membrane. It has been known for several years that high level expression of PGP is a mechanism for tumor resistance to cancer chemotherapy. Intestinal expression of PGP may affect the oral bioavailability of drug molecules that are substrates for this transporter. PGP can efficiently efflux drugs back into the intestinal lumen and thus reduce the amount of drug that enters into circulation.

The measurement of interaction with PGP can provide a better understanding of the reasons why particular drugs demonstrate low or high bioavailability. Interaction with PGP can be studied using either direct assays of drug transport in polarized cell systems or with indirect assays such as drug-stimulated ATPase activity and inhibition of the transport of fluorescent substrates.

Therefore there is a need for additional PGP polypeptides, preferably which are closely related to the human PGP, for use in the foregoing drug assays.

SUMMARY OF THE INVENTION

Nucleic acids encoding the P-glycoprotein of cynomologous monkey (*Macaca fascicularis*) have now been identified, isolated, cloned and sequenced. This PGP is closely related (has a high degree of identity) to the human PGP. The invention provides isolated nucleic acid molecules, unique fragments of those molecules, expression vectors containing the foregoing, and host cells transfected with those molecules. The invention also provides isolated polypeptides and inhibitors of the foregoing nucleic acids and polypeptides which reduce drug transport. The PGP nucleic acids and polypeptides are useful in assays for evaluating bioavailability of drugs, as well as for the optimization or discovery of drugs. In addition, the foregoing can be used in the diagnosis or treatment of conditions characterized by PGP activity and can be used in methods in which it is therapeutically useful to increase or decrease PGP activity.

According to one aspect of the invention, isolated nucleic acid molecules are provided selected from the group consisting of (a) nucleic acid molecules that code for the amino acid sequence of SEQ ID NO:2 or SEQ ID NO:4, (b) allelic variants of (a), and (c) complements of (a) or (b). In certain embodiments, the isolated nucleic acid molecule codes for SEQ ID NO:2 or SEQ ID NO:4. In other embodiments, the isolated nucleic acid molecule comprises the nucleotide sequence of SEQ ID NO:2 or SEQ ID NO:4.

According to another aspect of the invention, isolated P-glycoprotein polypeptides or fragments thereof are provided which include at least one amino acid of a cynomologous P-glycoprotein selected from the group consisting of amino acids 12, 24, 30, 74, 78, 86, 89, 90, 91, 92, 95, 97, 99, 102, 103, 104, 185, 324, 363, 518, 635, 650, 656, 659, 677, 730, 738, 742, 745, 761, 765, 835, 851, 921, 967, 1003, 1027, 1038, 1048, 1103, 1128, 1168 and 1277 of SEQ ID NO:2 and amino acids 93, 94 and 95 of SEQ ID NO:4, wherein the P-glycoprotein is identical to a human P-glycoprotein except for the at least one amino acid of a cynomologous P-glycoprotein. In certain embodiments, the human P-glycoprotein is selected from the group of SEQ ID NO:5 and SEQ ID NO:6.

According to yet another aspect of the invention, isolated P-glycoprotein polypeptides or fragments thereof which include at least one amino acid of a cynomologous P-glycoprotein selected from the group consisting of amino acids 3, 6, 8, 10, 13, 17, 19, 20, 21, 26, 30, 36, 38, 48, 52, 56, 64, 74, 78, 84, 85, 86, 87, 88, 89, 90, 91, 92, 93, 94, 95, 96, 98, 100, 101, 102, 103, 104, 105, 106, 110, 113, 145, 190, 197, 210, 231, 319, 324, 327, 345, 363, 395, 451, 455, 456, 468, 473, 494, 518, 530, 631, 641, 642, 648, 650, 655, 656, 664, 665, 672, 673, 674, 675, 683, 687, 689, 691, 692, 694, 701, 705, 715, 729, 730, 734, 742, 743, 745, 754, 757, 765, 835, 912, 918, 921, 940, 941, 944, 966, 967, 968, 970, 972, 981, 1008, 1015, 1023, 1024, 1048, 1093, 1096, 1103, 1128, 1142, 1146, 1147, 1156, 1160, 1163, 1166, 1250 and 1271 of SEQ ID NO:2 and amino acids 93 and 94 of SEQ ID NO:4, wherein the P-glycoprotein is identical to a dog P-glycoprotein except for the at least one amino acid of a cynomologous P-glycoprotein. In some embodiments, the dog P-glycoprotein is selected from the group of SEQ ID NO:7 and SEQ ID NO:8.

In preferred embodiments, the isolated P-glycoprotein polypeptides or fragments thereof include an amino acid sequence selected from the group consisting of SEQ ID NO:2, fragments of SEQ ID NO:2, SEQ ID NO:4 and fragments of SEQ ID NO:4. Yet other polypeptides include combinations of the foregoing dog, human and cynomologous PGP polypeptides.

According to still other embodiments of the invention, isolated nucleic acid molecules are provide which encode the foregoing isolated P-glycoprotein polypeptides or fragments thereof. Also included expression vectors comprising the foregoing isolated nucleic acid molecules operably linked to a promoter, as well as host cells transformed or transfected with the expression vectors.

In another aspect of the invention, agents which selectively binds the isolated PGP polypeptides are provided. Preferably the agent does not bind a human or dog P-glycoprotein, except those provided herein. In certain embodiments, the agent is a polypeptide preferably one selected from the group consisting of monoclonal antibodies, polyclonal antibodies, Fab antibody fragments, F(ab)$_2$ antibody fragments and antibody fragments including a CDR3 region. Also provided are agents which selectively binds the foregoing isolated nucleic acid molecules, preferably antisense nucleic acid molecules which selectively binds to the isolated nucleic acid molecule.

According to another aspect of the invention, methods for predicting the bioavailability of a compound are provided. The methods include measuring the transmembrane transport of a test compound by a first P-glycoprotein, comparing the transmembrane transport of the test compound by the first P-glycoprotein and a second P-glycoprotein to predict the bioavailability of the test compound, wherein the relative amount or rate of transport by the first P-glycoprotein and the second P-glycoprotein is predictive of bioavailability of the test compound. In certain embodiments the first P-glycoprotein is selected from the group consisting of dog P-glycoproteins and primate P-glycoproteins, preferably one of the foregoing polypeptides. In other embodiments the second P-glycoprotein is a human P-glycoprotein.

In still other aspects of the invention, methods for inhibiting P-glycoprotein transporter activity in a mammalian cell are provided. The methods include contacting the mammalian cell with an amount of one of the foregoing agents effective to inhibit P-glycoprotein transporter activity in the mammalian cell.

Also included in the invention are methods for increasing bioavailability of a drug in a subject. The methods include administering to a subject in need of such treatment one of the foregoing agents in an amount effective to increasing bioavailability of a drug. The inhibitor can be administered prior to administering the drug, or concurrently with the drug.

Also provided are methods for increasing P-glycoprotein transporter activity in a cell. These methods include contacting the cell with a molecule selected from the group consisting of the foregoing nucleic acid molecules, in an amount effective to increase P-glycoprotein transporter activity in the cell. The cell can be contacted under conditions whereby the P-glycoprotein is expressed.

According to yet another aspect of the invention, methods for identifying lead compounds for a pharmacological agent useful in the treatment of disease associated with P-glycoprotein transporter activity are provided. The methods include providing a cell or other membrane-encapsulated space comprising a P-glycoprotein as provided herein; contacting the cell or other membrane-encapsulated space with a candidate pharmacological agent under conditions which, in the absence of the candidate pharmacological agent, cause a first amount of P-glycoprotein transporter activity; and determining a second amount of P-glycoprotein transporter activity as a measure of the effect of the pharmacological agent on the P-glycoprotein transporter activity, wherein a second amount of P-glycoprotein transporter activity which is less than the first amount indicates that the candidate pharmacological agent is a lead compound for a pharmacological agent which reduces P-glycoprotein transporter activity and wherein a second amount of P-glycoprotein transporter activity which is greater than the first amount indicates that the candidate pharmacological agent is a lead compound for a pharmacological agent which increases P-glycoprotein transporter activity. The methods can further include a step of loading the cell or other membrane-encapsulated space with a detectable compound, wherein the compound is detected as a measure of the P-glycoprotein transporter activity.

Also included are methods for identifying compounds which selectively bind a P-glycoprotein. The methods include contacting a P-glycoprotein provided herein with a compound, and determining the binding of the compound to the P-glycoprotein. The methods can further include determining the effect of the compound on the P-glycoprotein transporter activity of the P-glycoprotein or determining the effect of the compound on the ATPase activity of the P-glycoprotein.

Additional methods provided according to the invention include methods for determining ATPase activity of a P-glycoprotein. The methods include contacting a host cell as provided above, or a membrane fraction thereof, with a test drug, and measuring ATPase activity of the P-glycoprotein. In certain embodiments, the step of measuring ATPase activity is performed at least twice at different times. Also provided methods for determining to transmembrane transport of a compound by a P-glycoprotein. The methods include contacting a host cell provided above, or a membrane fraction thereof, with a test drug, and measuring transport of the test drug under sink conditions in at least one direction of transport selected from the group consisting of the apical to basolateral direction and the basolateral to apical direction. In certain embodiments the step of measuring transport of the test drug is performed at least twice at different times.

These and other aspects of the invention are described in greater detail below.

BRIEF DESCRIPTION OF THE SEQUENCES

SEQ ID NO:1 is the nucleotide sequence encoding cynomologous monkey P-glycoprotein.

SEQ ID NO:2 is the amino acid sequence of a cynomologous monkey P-glycoprotein encoded by SEQ ID NO:1.

SEQ ID NO:3 is the nucleotide sequence of a cynomologous monkey P-glycoprotein allele having a 9 nucleotide insert relative to SEQ ID NO:1.

SEQ ID NO:4 is the amino acid sequence of a cynomologous monkey P-glycoprotein allelic variant encoded by SEQ ID NO:3, having a 3 amino acid insert.

SEQ ID NO:5 is the amino acid sequence of a human P-glycoprotein having Genbank accession number M14758.

SEQ ID NO:6 is the amino acid sequence of a human P-glycoprotein having Genbank accession numbers AF016535 or NM_000927.

SEQ ID NO:7 is the amino acid sequence of a dog P-glycoprotein having Genbank accession number AF045016.

SEQ ID NO:8 is the amino acid sequence of a dog P-glycoprotein having Genbank accession numbers AF092810.

SEQ ID NO:9 is the nucleotide sequence of a primer based on the human PGP nucleotide sequence.

SEQ ID NO:10 is the nucleotide sequence of a primer based on the human PGP nucleotide sequence.

SEQ ID NO:11 is the nucleotide sequence of a primer based on the human PGP nucleotide sequence.

SEQ ID NO:12 is the nucleotide sequence of a primer based on the cynomologous PGP nucleotide sequence.

SEQ ID NO:13 is the nucleotide sequence of a primer based on the cynomologous PGP nucleotide sequence.

SEQ ID NO:14 is the nucleotide sequence of a primer based on the T7 promoter nucleotide sequence.

SEQ ID NO:15 is the nucleotide sequence of a primer based on the cynomologous and human PGP nucleotide sequences.

SEQ ID NO:16 is the nucleotide sequence of a primer based on the cynomologous and human PGP nucleotide sequences.

SEQ ID NO:17 is the nucleotide sequence of a primer based on the cynomologous PGP nucleotide sequence.

SEQ ID NO:18 is the nucleotide sequence of a primer based on the cynomologous PGP nucleotide sequence.

DETAILED DESCRIPTION OF THE INVENTION

The present invention in one aspect involves the identification of cDNAs encoding cynomologous monkey P-glycoproteins, referred to herein as cynomologous PGP. The nucleotide sequences of the cynomologous PGP are presented as SEQ ID Nos:1 and 3, and the amino acid sequences of the cynomologous PGP are presented as SEQ ID Nos:2 and 4. The nucleotide and amino acid sequences of a cynomologous PGP allelic variant (SEQ ID NOS:3 and 4) have inserts of 9 nucleotides and 3 amino acids, respectively, but are otherwise identical to SEQ ID NOS:1 and 2. The closely related human PGP was deposited in GenBank under accession number M14758. Whereas much of the polypeptides presented herein is identical to human PGP, cynomologous PGP has several single amino acid differences and a N-terminal domain of about 19–34 amino acids that is about 36–58% identical to human PGP. The insert present in the allelic variant referred to above (SEQ ID NOS:3 and 4) is located near the end of this cynomologous-specific domain. Surprisingly, the N-terminal domain of the cynomologous PGP that differs from the human amino acid sequence is located in a portion of the molecule in which the cynomologous and human amino acid sequences are otherwise 100% identical. This species difference in the very highly conserved protein domains of the P-glycoprotein is entirely unexpected.

The invention involves in one aspect cynomologous PGP nucleic acids and polypeptides, as well as therapeutics relating thereto. The invention also embraces isolated functionally equivalent variants, useful analogs and fragments of the foregoing nucleic acids and polypeptides; complements of the foregoing nucleic acids; and molecules which selectively bind the foregoing nucleic acids and polypeptides.

The cynomologous PGP nucleic acids and polypeptides of the invention are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

As used herein a cynomologous PGP nucleic acid refers to an isolated nucleic acid molecule which codes for a cynomologous PGP polypeptide. Such nucleic acid molecules code for cynomologous PGP polypeptides which include the sequence of SEQ ID NOs:2 and 4, and fragments thereof. The nucleic acid molecules include the nucleotide sequences of SEQ ID Nos:1 and 3, and nucleotide sequences which differ from the sequences of SEQ ID NOs:1 and 3 in codon sequence due to the degeneracy of the genetic code. The cynomologous PGP nucleic acids of the invention also include alleles of the foregoing nucleic acids, as well as fragments of the foregoing nucleic acids. Such fragments can be used, for example, as probes in hybridization assays and as primers in a polymerase chain reaction (PCR). Preferred cynomologous PGP nucleic acids include the nucleic acid sequence of SEQ ID NO:1 or SEQ ID NO:3. Complements of the foregoing nucleic acids also are embraced by the invention.

As used herein "cynomologous PGP activity" refers to an ability of a PGP polypeptide to export small molecules across the cell membrane. A molecule which inhibits cynomologous PGP activity (an antagonist) is one which inhibits export of small molecules via PGP and a molecule which increases cynomologous PGP activity (an agonist) is one which increases export of small molecules via PGP. Changes in cynomologous PGP activity can be measured by assays such as those disclosed herein, including efflux of fluorescent compounds from cells.

Alleles of the cynomologous PGP nucleic acids of the invention can be identified by conventional techniques. For example, alleles of cynomologous PGP can be isolated by hybridizing a probe which includes at least a fragment of SEQ ID NO:1 or SEQ ID NO:3 under stringent conditions with a cDNA library and selecting positive clones. Thus, an aspect of the invention is those nucleic acid sequences which code for cynomologous PGP polypeptides and which hybridize to a nucleic acid molecule consisting of SEQ ID NO:1 or SEQ ID NO:3 under stringent conditions. The term "stringent conditions" as used herein refers to parameters with which the art is familiar. Nucleic acid hybridization parameters may be found in references which compile such methods, e.g. Molecular Cloning: *A Laboratory Manual, J. Sambrook*, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5mM $NaH_2PO_4$(pH7), 0.5% SDS, 2mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1–0.5×SSC/0.1× SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of alleles of cynomologous PGP nucleic acids of the invention. The skilled artisan also is familiar with the methodology for screening cells and libraries for expression of such molecules which then are routinely isolated, followed by isolation of the pertinent nucleic acid molecule and sequencing.

In screening for cynomologous PGP nucleic acids, a Southern blot may be performed using the foregoing stringent conditions, together with a radioactive probe. After washing the membrane to which the DNA is finally transferred, the membrane can be placed against X-ray film to detect the radioactive signal.

The cynomologous PGP nucleic acids of the invention also include degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating cynomologous PGP polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as transporter activity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated fragments of SEQ ID NO:1 and SEQ ID NO:3. The fragments can be used as probes in Southern blot assays to identify such nucleic acids, or can be used in amplification assays such as those employing PCR. Smaller fragments are those comprising 12, 13, 14, 15, 16, 17, 18, 20, 22, 25, 30, 40, 50, or 75 nucleotides, and every integer therebetween, and are useful e.g. as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the cynomologous PGP polypeptides, useful, for example, in the preparation of antibodies, in immunoassays, and the like. The foregoing nucleic acid fragments further can be used as antisense molecules to inhibit the expression of cynomologous PGP nucleic acids and polypeptides, particularly for therapeutic purposes as described in greater detail below.

The invention also includes functionally equivalent variants of the cynomologous PGP, which include variant nucleic acids and polypeptides which retain one or more of the functional properties of the cynomologous PGP. Preferably such variants include the cynomologous-specific N-terminal domain (e.g., amino acids 86–104 of SEQ ID NO:2 or amino acids 86–101 of SEQ ID NO:4). For example, variants include a fusion protein which includes the extracellular and transmembrane domains of the cynomologous PGP which retains the ability to transport molecules. Still other functionally equivalent variants include truncations, deletions, point mutations, or additions of amino acids to the sequence of SEQ ID NOs:2 or 4 which retain functions of SEQ ID NOs:2 or 4. Functionally equivalent variants also include a cynomologous PGP which has had a portion of the N-terminus removed or replaced by a similar domain from another P-glycoprotein (e.g. a "domain-swapping" variant). Other functionally equivalent variants will be known to one of ordinary skill in the art, as will methods for preparing such variants. The activity of a functionally equivalent variant can be determined using the methods provided herein, and in references that have described assays using P-glycoproteins of other species. Such variants are useful, inter alia, for evaluating bioavailability of drugs, in assays for identification of compounds which bind and/or regulate the transporter function of the cynomologous PGP, and for determining the portions of the cynomologous PGP which are required for transporter activity.

Variants which are non-functional also can be prepared as described above. Such variants are useful, for example, as negative controls in experiments testing transporter activity.

A cynomologous PGP nucleic acid, in one embodiment, is operably linked to a gene expression sequence which directs the expression of the cynomologous PGP nucleic acid within a eukaryotic or prokaryotic cell. The "gene expression sequence" is any regulatory nucleotide sequence, such as a promoter sequence or promoter-enhancer combination, which facilitates the efficient transcription and translation of the cynomologous PGP nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney murine leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined cynomologous PGP nucleic acid. The gene expression sequences optionally includes enhancer sequences or upstream activator sequences as desired.

The cynomologous PGP nucleic acid sequence and the gene expression sequence are said to be "operably linked" when they are covalently linked in such a way as to place the transcription and/or translation of the cynomologous PGP coding sequence under the influence or control of the gene expression sequence. If it is desired that the cynomologous PGP sequence be translated into a functional protein, two DNA sequences are said to be operably linked if induction of a promoter in the 5' gene expression sequence results in the transcription of the cynomologous PGP sequence and if the nature of the linkage between the two DNA sequences does not (1) result in the introduction of a frame-shift mutation, (2) interfere with the ability of the promoter region to direct the transcription of the cynomologous PGP sequence, or (3) interfere with the ability of the corresponding RNA transcript to be translated into a protein. Thus, a gene expression sequence would be operably linked to a cynomologous PGP nucleic acid sequence if the gene expression sequence were capable of effecting transcription of that cynomologous PGP nucleic acid sequence such that the resulting transcript might be translated into the desired protein or polypeptide.

The cynomologous PGP nucleic acid molecules and the cynomologous PGP polypeptides (including the cynomologous PGP inhibitors described below) of the invention can be delivered to the eukaryotic or prokaryotic cell alone or in association with a vector. In its broadest sense, a "vector" is any vehicle capable of facilitating: (1) delivery of a cynomologous PGP nucleic acid or polypeptide to a target cell, (2) uptake of a cynomologous PGP nucleic acid or polypeptide by a target cell, or (3) expression of a cynomologous PGP nucleic acid molecule or polypeptide in a target cell. Preferably, the vectors transport the cynomologous PGP nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor (e.g. a receptor, an antigen recognized by an antibody) for the targeting ligand. In this manner, the vector (containing a cynomologous PGP nucleic acid or a cynomologous PGP polypeptide) can be selectively delivered to a specific cell. In general, the vectors useful in the invention are divided into two classes: biological vectors and chemical/physical vectors. Biological vectors are more useful for delivery/uptake of cynomologous PGP nucleic acids to/by a target cell. Chemical/physical vectors are more useful for delivery/uptake of cynomologous PGP nucleic acids or cynomologous PGP proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be linked to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenovirus; adeno-associated virus; SV40-type viruses; polyoma viruses; poxyiruses; retroviruses; Epstein-Barr viruses; papilloma viruses; herpes virus; vaccinia virus; and polio virus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual,* " W. H. Freeman C. O., New York (1990) and Murry, E. J. Ed. "*Methods in Molecular Biology,* " vol. 7, Humana Press, Inc., Clifton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a cynomologous PGP polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992).

In addition to the biological vectors, chemical/physical vectors may be used to deliver a cynomologous PGP nucleic acid or polypeptide to a target cell and facilitate uptake thereby. As used herein, a "chemical/physical vector" refers to a natural or synthetic molecule, other than those derived from bacteriological or viral sources, capable of delivering the isolated cynomologous PGP nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as a delivery vector in vivo or in vitro. It has been shown that large unilamellar vesicles (LUV), which range in size from 0.2–4.0μ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the cynomologous PGP nucleic acid to the nucleus of the host cell.

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

Other exemplary compositions that can be used to facilitate uptake by a target cell of the cynomologous PGP nucleic acids include calcium phosphate and other chemical mediators of intracellular transport, microinjection compositions, electroporation and homologous recombination compositions (e.g., for integrating a cynomologous PGP nucleic acid into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of the cynomologous PGP cDNA sequences in expression vectors, as well as to transfect host cells and cell lines, be these prokaryotic (e.g., *E. coli*), or eukaryotic (e.g., COS cells, yeast expression systems and recombinant baculovirus expression in insect cells). Especially useful are mammalian cells such as human, pig, goat, primate, etc. They may be of a wide variety of tissue types, and include primary cells and cell lines. Specific examples include intestinal cells and liver cells. The expression vectors require that the pertinent sequence, i.e., those nucleic acids described supra, be operably linked to a promoter.

The invention also provides isolated cynomologous PGP polypeptides which include the amino acid sequences of SEQ ID NO:2 and SEQ ID NO:4, and fragments thereof, encoded by the cynomologous PGP nucleic acids described above. Cynomologous PGP polypeptides also embrace alleles, functionally equivalent variants and analogs (those non-allelic polypeptides which vary in amino acid sequence from the disclosed cynomologous PGP polypeptides by 1, 2, 3, 4, 5, or more amino acids) provided that such polypeptides retain cynomologous PGP activity. Non-functional variants also are embraced by the invention; these are useful as antagonists of transporter function, as negative controls in assays, and the like. Such alleles, variants, analogs and fragments are useful, for example, alone or as fusion proteins for a variety of purposes including as a component of assays.

Fragments of a polypeptide preferably are those fragments which retain a distinct functional capability of the cynomologous PGP polypeptide, in particular as a transporter of various molecules. Other functional capabilities which can be retained in a fragment of a cynomologous PGP polypeptide include interaction with antibodies and interaction with other polypeptides (such as would be found in a protein complex). Those skilled in the art are well versed in methods for selecting fragments which retain a functional capability of the cynomologous PGP. Confirmation of the functional capability of the fragment can be carried out by synthesis of the fragment and testing of the capability according to standard methods. For example, to test the transporter activity of a cynomologous PGP fragment, one inserts or expresses the fragment in a cell in which molecular transport can be measured. Such methods, which are standard in the art, are described further herein.

The invention embraces variants of the cynomologous PGP polypeptides described above. As used herein, a "variant" of a cynomologous PGP polypeptide is a polypeptide which contains one or more modifications to the primary amino acid sequence of a cynomologous PGP polypeptide. Modifications which create a cynomologous PGP variant can be made to a cynomologous PGP polypeptide for a variety of reasons, including 1) to reduce or eliminate an activity of a cynomologous PGP polypeptide, such as transport; 2) to enhance a property of a cynomologous PGP polypeptide, such as protein stability in an expression system or the stability of protein-protein binding; 3) to provide a novel activity or property to a cynomologous PGP polypeptide, such as addition of an antigenic epitope or addition of a detectable moiety; or 4) to establish that an amino acid substitution does or does not affect molecular transport activity. Modifications to a cynomologous PGP polypeptide are typically made to the nucleic acid which encodes the cynomologous PGP polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the cynomologous PGP amino acid sequence. One of skill in the art will be familiar with methods for predicting the effect on protein conformation of a change in protein sequence, and can thus "design" a variant cynomologous PGP according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cynomologous PGP polypeptide can be proposed and tested to determine whether the variant retains a desired conformation.

Variants include cynomologous PGP polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a cynomologous PGP polypeptide by eliminating proteolysis by proteases in an expression system (e.g., dibasic amino acid residues in yeast expression systems in which KEX2 protease activity is present).

Mutations of a nucleic acid which encode a cynomologous PGP polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant cynomologous PGP polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a cynomologous PGP gene or cDNA clone to enhance expression of the polypeptide.

The activity of variants of cynomologous PGP polypeptides can be tested by cloning the gene encoding the variant cynomologous PGP polypeptide into a bacterial or mammalian expression vector, introducing the vector into an appropriate host cell, expressing the variant cynomologous PGP polypeptide, and testing for a functional capability of the cynomologous PGP polypeptides as disclosed herein. For example, the variant cynomologous PGP polypeptide can be tested for ability to provide molecular transport (e.g., efflux), as set forth below in the examples. Preparation of other variant polypeptides may favor testing of other activities, as will be known to one of ordinary skill in the art.

The skilled artisan will also realize that conservative amino acid substitutions may be made in cynomologous PGP polypeptides to provide functionally equivalent variants of the foregoing polypeptides, i.e, variants which retain the functional capabilities of the cynomologous PGP polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the cynomologous PGP polypeptides include conservative amino acid substitutions of SEQ ID NO:2 or SEQ ID NO:4. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of cynomologous PGP polypeptide to produce functionally equivalent variants of cynomologous PGP typically are made by alteration of the nucleic acid sequence encoding cynomologous PGP polypeptides (e.g., SEQ ID NOs:1 or 3). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a cynomologous PGP polypeptide. The activity of functionally equivalent fragments of cynomologous PGP polypeptides can be tested by cloning the gene encoding the altered cynomologous PGP polypeptide into a bacterial or mammalian expression vector, introducing the vector into an appropriate host cell, expressing the altered cynomologous PGP polypeptide, and testing for the ability of the cynomologous PGP polypeptide to mediate transmembrane transport of compounds. Peptides which are chemically synthesized can be tested directly for function.

A variety of methodologies well-known to the skilled practitioner can be utilized to obtain isolated cynomologous PGP molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the[]art also can readily follow known methods for isolating cynomologous PGP polypeptides. These include, but are not limited to, immunochromatography, HPLC, size-exclusion chromatography, ion-exchange chromatography and immune-affinity chromatography.

The invention as described herein has a number of uses, some of which are described elsewhere herein. For example, the invention permits isolation of the cynomologous PGP polypeptide molecules by e.g., expression of a recombinant nucleic acid to produce large quantities of polypeptide which may be isolated using standard protocols. As another example, the isolation of the cynomologous PGP gene makes it possible for cynomologous PGP to be used in methods for assaying of molecular transport, such as drug bioavailability studies. These methods involve determining transport of a drug by a first species' PGP (e.g., cynomologous, dog) in comparison to transport of the drug by other species' PGP (e.g. human) as a method for determining or predicting the bioavailability of the drug. Thus the results of whole animal studies on the metabolism of a drug can be evaluated in view of the relative rates or amounts of P-glycoprotein transport of the drug. For example, if a drug administered to a dog has good oral bioavailability and low transport by dog PGP, one can predict that the oral bioavailability of the drug in humans will be good if the transport by human PGP is also low. Conversely, if the transport of the drug by human PGP is high, then the bioavailability of the drug would be predicted to be low.

The invention also embraces agents which bind selectively to the cynomologous PGP nucleic acid molecules or polypeptides as well as agents which bind to variants and fragments of the polypeptides and nucleic acids as described herein. The agents include polypeptides which bind to cynomologous PGP, and antisense nucleic acids, both of which are described in greater detail below. The agents can inhibit or increase cynomologous PGP activity (antagonists and agonists, respectively).

Some of the agents are inhibitors. A cynomologous PGP inhibitor is an agent that inhibits cynomologous PGP mediated transport of molecules across a cell membrane. Efflux assays can be performed to screen and/or determine whether a cynomologous PGP inhibitor has the ability to inhibit cynomologous PGP activity, and whether the inhibition is selective. An exemplary assay of efflux is described below in the Examples.

In one embodiment the cynomologous PGP inhibitor is an antisense oligonucleotide that selectively binds to a cynomologous PGP nucleic acid molecule, to reduce the expression of cynomologous PGP (or other species's PGPs) in a cell. This is desirable in virtually any medical condition wherein a reduction of PGP transporter activity is desirable, e.g., to increase retention of cytotoxic agents in a cell.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NOs:1 or 3, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which polypeptides are not expected to bind. Thus, the present invention also provides for antisense oligonucleotides which are complementary to allelic or homologous cDNAs and genomic DNAs corresponding to cynomologous PGP nucleic acid containing SEQ ID NOs: 1 or 3.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic intemucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic intemucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding cynomologous PGP polypeptides, together with pharmaceutically acceptable carriers.

Agents which bind cynomologous PGP also include binding peptides and other molecules which bind to the cynomologous PGP polypeptide and complexes containing the cynomologous PGP polypeptide. When the binding molecules are inhibitors, the molecules bind to and inhibit the activity of cynomologous PGP. To determine whether a cynomologous PGP binding agent binds to cynomologous PGP any known binding assay may be employed. For example, the binding agent may be immobilized on a surface and then contacted with a labeled cynomologous PGP polypeptide. The amount of cynomologous PGP which interacts with the cynomologous PGP binding agent or the amount which does not bind to the cynomologous PGP binding agent may then be quantitated to determine whether the cynomologous PGP binding agent binds to cynomologous PGP.

The cynomologous PGP binding agents include molecules of numerous size and type that bind selectively or preferentially to cynomologous PGP polypeptides, and complexes of both cynomologous PGP polypeptides and their binding partners. These molecules may be derived from a variety of sources. For example, cynomologous PGP binding agents can be provided by screening degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cynomologous PGP polypeptide. This process can be repeated through several cycles of reselection of phage that bind to the cynomologous PGP polypeptide. Repeated rounds lead to enrichment of phage bearing particular sequences. DNA sequence analysis can be conducted to identify the sequences of the expressed polypeptides. The minimal linear portion of the sequence that binds to the cynomologous PGP polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cynomologous PGP polypeptides. Thus, the cynomologous PGP polypeptides of the invention, or a fragment thereof, can be used to screen peptide libraries, including phage display libraries, to identify and select peptide binding partners of the cynomologous PGP polypeptides of the invention. Such molecules can be used, as described, for screening assays, for purification protocols, for interfering directly with the functioning of cynomologous PGP and for other purposes that will be apparent to those of ordinary skill in the art.

Therefore the invention generally provides efficient methods of identifying pharmacological agents or lead compounds for agents useful in the treatment of conditions associated with aberrant PGP activity and the compounds and agents so identified. Generally, the screening methods involve assaying for compounds which inhibit or enhance transport of molecules through cynomologous PGP. Such methods are adaptable to automated, high throughput screening of compounds. Examples of such methods are described in U.S Pat. No. 5,429,921.

A variety of assays for pharmacological agents are provided, including, labeled in vitro protein binding assays, efflux assays using detectable molecules, etc. For example, protein binding screens are used to rapidly examine the binding of candidate pharmacological agents to a cynomologous PGP. The candidate pharmacological agents can be derived from, for example, combinatorial peptide libraries. Convenient reagents for such assays are known in the art. An exemplary cell-based assay of efflux involves contacting a cell having a cynomologous PGP with a candidate pharmacological agent under conditions whereby the efflux of a detectably labeled molecule can occur. Specific conditions are well known in the art and are described, for example, in Sharom et al., *Biochem. Pharmacol.* 58:571–586, 1999, and references cited therein. A reduction in the efflux in the presence of the candidate pharmacological agent indicates that the candidate pharmacological agent reduces the efflux activity of cynomologous PGP. An increase in the efflux in the presence of the candidate pharmacological agent indicates that the candidate pharmacological agent increases the efflux activity of cynomologous PGP.

Cynomologous PGP used in the methods of the invention can be added to an assay mixture as an isolated polypeptide (where binding of a candidate pharmaceutical agent is to be measured) or as a cell or other membrane-encapsulated space which includes a cynomologous PGP polypeptide. In the latter assay configuration, the cell or other membrane-encapsulated space can contain the cynomologous PGP as a preloaded polypeptide or as a nucleic acid (e.g. a cell transfected with an expression vector containing a cynomologous PGP). In the assays described herein, the cynomologous PGP polypeptide can be produced recombinantly, or isolated from biological extracts, but preferably is synthesized in vitro. Cynomologous PGP polypeptides encompass chimeric proteins comprising a fusion of a cynomologous PGP polypeptide with another polypeptide, e.g., a polypeptide capable of providing or enhancing protein-protein binding, or enhancing stability of the cynomologous PGP polypeptide under assay conditions. A polypeptide fused to a cynomologous PGP polypeptide or fragment thereof may also provide means of readily detecting the fusion protein, e.g., by immunological recognition or by fluorescent labeling.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

Therefore, a source of candidate agents are libraries of molecules based on known P-glycoprotein inhibitors, in which the structure of the inhibitor is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on existing P-glycoprotein inhibitors.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate pharmacological agent, the cynomologous PGP mediates the efflux of a control amount of a compound such as a drug. For determining the binding of a candidate pharmaceutical agent to a cynomologous PGP, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of efflux or the level of specific binding between the cynomologous PGP polypeptide and the candidate pharmaceutical agent is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a transmembrane transport assay. The transport of a directly or indirectly detectable product, e.g., a fluorescent molecule such as calcein AM or rhodamine 123, is preferred. For cell free binding assays, one of the components usually comprises, or is coupled to, a detectable label. A wide variety of labels can be used, such as those that provide direct detection (e.g., to radioactivity, luminescence, optical or electron density, etc). or indirect detection (e.g., epitope tag such as the FLAG epitope, enzyme tag such as horseradish peroxidase, etc.). The label may be bound to a cynomologous PGP polypeptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The cynomologous PGP binding agent may also be an antibody or a functionally active antibody fragment. Antibodies are well known to those of ordinary skill in the science of immunology. As used herein, the term "antibody" means not only intact antibody molecules but also fragments of antibody molecules retaining cynomologous PGP binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316–325 (1983)).

Monoclonal antibodies may be made by any of the methods known in the art utilizing cynomologous PGP, or a fragment thereof, as an immunogen. Alternatively the antibody may be a polyclonal antibody specific for cynomologous PGP which inhibits cynomologous PGP activity. The preparation and use of polyclonal antibodies is also known to one of ordinary skill in the art.

Significantly, as is well known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, 1. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3).

The CDRs, and in particular the CDR3 regions, and more particularly the heavy chain CDR3, are largely responsible for antibody specificity.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to antigen epitopes.

The sequences of the antigen-binding Fab' portion of the anti-cynomologous PGP monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit cynomologous PGP activity are identified. These non-human animal antibodies can be humanized for use in the treatment of a human subject in the methods according to the invention. Examples of methods for humanizing a murine antibody are provided in U.S. Pat. Nos. 4,816,567, 5,225,539, 5,585,089, 5,693,762 and 5,859, 205. Other antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-cynomologous PGP monoclonal antibody; chimeric antibodies in which the Fc and/or FR and/or CDR1 and/or CDR2 and/or light chain CDR3 regions of an anti-cynomologous PGP antibody have been replaced by homologous human or non-human sequences; chimeric F(ab')$_2$ fragment antibodies in which the FR and/or CDR1 and/or CDR2 and/or light chain CDR3 regions of an anti-cynomologous PGP antibody have been rep laced by homologous human or non-human sequences; and chimeric Fab fragment antibodies in which the FR and/or CDR1 and/or CDR2 and/or light chain CDR3 regions have been replaced by homologous human or non-human sequences.

According to the invention cynomologous PGP inhibitors also include "dominant negative" polypeptides derived from SEQ ID NOs:2 or 4. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the ligand.

The end result of the expression of a dominant negative cynomologous PGP polypeptide of the invention in a cell is a reduction in PGP activity such as molecular transport. One of ordinary skill in the art can assess the potential for a dominant negative variant of a cynomologous PGP polypeptide, and using standard mutagenesis techniques to create one or more dominant negative variant polypeptides. For example, given the teachings contained herein of a cynomologous PGP polypeptide, one of ordinary skill in the art can modify the sequence of the cynomologous PGP polypeptide by site-specific mutagenesis, scanning mutagenesis, partial gene deletion or truncation, and the like. See, e.g., U.S. Pat. No. 5,580,723 and Sambrook et al., *Molecular Cloning. A Laboratory Manual*, Second Edition, Cold Spring Harbor Laboratory Press, 1989. The skilled artisan then can test the population of mutagenized polypeptides for diminution in cynomologous PGP activity and/or for retention of such an activity. Other similar methods for creating and testing dominant negative variants of a cynomologous PGP polypeptide will be apparent to one of ordinary skill in the art.

Each of the compositions of the invention is useful for a variety of therapeutic and non-therapeutic purposes. For example, the cynomologous PGP nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, many labels useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci.* (USA) 80:4045 (1983); Renz, M. et al., *Nucl. Acids Res.* 12:3435 (1984); and Renz, M., *EMBO J.* 6:817 (1983).

Additionally, complements of the cynomologous PGP nucleic acids can be useful as antisense oligonucleotides, e.g., by delivering the antisense oligonucleotide to an animal to induce a cynomologous PGP "knockout" phenotype. The administration of antisense RNA probes to block gene expression is discussed in Lichtenstein, C., *Nature* 333:801–802 (1988).

Alternatively, the cynomologous PGP nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of cynomologous PGP knockout and transgenic animals as models for the study of disorders involving transport of molecules across cell membranes. A variety of methods known to one of ordinary skill in the art are available for the production of transgenic animals associated with this invention.

Inactivation or replacement of the endogenous PGP/ MDR1 gene can be achieved by a homologous recombination system using embryonic stem cells. The resultant transgenic non-human mammals having a PGP$^{-/-}$knockout phenotype may be made transgenic for the cynomologous PGP and used as a model for screening compounds as modulators (agonists or antagonists/inhibitors) of the cynomologous PGP. In this manner, such therapeutic drugs can be identified.

Additionally, a normal or mutant version of cynomologous PGP can be inserted into the germ line to produce transgenic animals which constitutively or inducibly express the normal or mutant form of cynomologous PGP. These animals are useful in studies to define the role and function of cynomologous PGP in cells.

The compositions of the invention are also useful for therapeutic purposes. Accordingly the invention encompasses a method for inhibiting cynomologous PGP activity in a mammalian cell. The invention further provides methods for reducing or increasing cynomologous PGP activity in a cell. In one embodiment, the method involves contacting the mammalian cell with an amount of a cynomologous PGP nucleic acid or polypeptide effective to inhibit molecular transport out of the mammalian cell. Such methods are useful in vitro for the purpose of, for example, elucidating the mechanisms involved in drug resistance and reduced drug bioavailability.

The invention also encompasses a method for increasing PGP expression in a cell or subject. The amount of cynomologous PGP can be increased in such cell or subject by contacting the cell with, or administering to the subject, a PGP nucleic acid or a PGP polypeptide of the invention to the subject in an amount effective to increase transmembrane transport in the cell or the subject. An increase in PGP activity can be measured by the assays described herein, e.g., assays of transmembrane transport.

The preparations of the invention are administered in effective amounts. An effective amount is that amount of a pharmaceutical preparation that alone, or together with further doses, produces the desired response. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Generally, doses of active compounds would be from about 0.01 mg/kg per day to 1000 mg/kg per day. It is expected that doses ranging from 50–500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compound, although fewer doses typically will be given when compounds are prepared as slow release or sustained release medications.

When administered, the pharmaceutical preparations of the invention are applied in pharmaceutically-acceptable amounts and in pharmaceutically-acceptably compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The cynomologous PGP inhibitors or cynomologous PGP nucleic acids and polypeptides useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intrathecal, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the cynomologous PGP inhibitor or cynomologous PGP nucleic acids and polypeptides, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intrathecal, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art. Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Example 1

Isolation of Cynomologous Monkey P-glycoprotein cDNA libraries were prepared using cynomologous monkey (*Macaca fascicularis*) mRNA according to standard procedures. The libraries were screened for P-glycoprotein clones using a human P-glycoprotein DNA probe. Clones were isolated, purified and sequenced in accordance with standard procedures.

Preparation of Library

A custom Lambda ZAP II cDNA library from Cynamologous monkey liver was prepared by Stratagene. This template was used to obtain clones 72/73 and 79/77 1500.

Anticipating that the monkey would show substantial homology to the human PGP, initial primers were designed from the human PGP (Genbank Accession Number M14758). Primers were also made based on the Lambda ZAP II vector sequences. Later primers were designed based on the monkey sequence or a combination of the monkey/human sequences. All primers used are listed below.

| Primer Sequence | Source | SEQ NO | nucleotides |
|---|---|---|---|
| PS070 ctg gac ttc ctc tca tga tgc tgg tgt | Human PGP | 9 | 612–638 F |
| PS072 gac agc tat tcg aag agt ggg cac aaa c | " | 10 | 1550–1577 F |
| PS073 ggc cat ggc acc aaa gac aac agc | " | 11 | 3362–3385 R |
| PS074 ttg gac aca gaa agt gaa gca gt | Cyno Monkey PGP | 12 | 2105–2127 F (human seq) |
| PS075 ctg agc atg gat cgg aaa ac | Cyno Monkey PGP | 13 | 2798–2817 R (human seq) |
| PS077 ttg taa tac gac tca cta tag ggc gaa t | T7 primer | 14 | "Based on Stratagene's seq. |
| PS078 ctt ttc gag atg ggt aac tga agt gaa c | Cyno/human PGP | 15 | 1613–1641 R |
| PS079 aga agg tgc tgg gaa gat cgc tac tga a | Cyno/human PGP | 16 | 3094–3121 F |
| PS080 gcc taa agc cga aca cat | Cyno Monkey PGP | 17 | 3498–3515 F |
| PS081 cta tta agt ctg cat tct gga | Cyno Monkey PGP | 18 | 4134–4154 R |

All PCR reactions were done using a Perkin Elmer 9700 Thermocycler. PCR products were analyzed on an agarose gel, and promising bands were purified by the use of Qiaquick Gel Extraction Kit (Qiagen) according to the manufacturer's instructions. These bands were ligated into pCR 2.1 and transformed into INVaF using Invitrogen's TA Cloning protocol according to the manufacturer's instructions. White colonies were picked and analyzed by restriction digest. DNA was prepared from promising clones using the Promega Wizard Plus Miniprep DNA Purification System according to the manufacturer's instructions and sequenced with an ABI 377 sequencer.

Clone 72/73

Using primers ps072 and ps073, a ~1.8 kb fragment was obtained following 38 cycles of PCR (94° C. for 5 m; followed by 38 cycles of 94° for 30 s, 63° C. for 45 s, 72° C. for 60 s; ending with 72° C. for 7 m) using Klentaq. This was sequenced using m13F and m13R primers. Further sequencing primers, ps074 and ps075 were designed based on the sequence obtained. This resulted in a total of ~1.85 kb sequenced corresponding to human PGP 1553–3361.

Clone 79/77 C1500

Using primers ps079 and ps077, a ~1.5 kb fragment was obtained following 38 cycles of PCR (94° C. for 5 m; followed by 38 cycles of 94° C. for 30 s, 63° C. for 45 s, 72° C. for 60 s; ending with 72° C. for 7 m) using Klentaq. This was sequenced using m13F and m13R as primers. Further sequencing primers, ps080 and ps081 were designed based on the sequence obtained. Sequence corresponding to the human pgp 3102–4525 was obtained, which included the stop codon for the cynomologous monkey PGP cDNA.

Clone 70/78C

Nucleobond RNA Maxi kit from Clontech was used according to the manufacturers to prepare total RNA from Cynomologous monkey liver. Single stranded cDNA was prepared from this RNA using the Superscript Kit from GIBCO BRL Life Technologies according to the manufacturer's instructions. This was used as a template for clones 70/78C. Using primers ps070 and ps078, a ~1.0 kb fragment was obtained from the liver cDNA following 38 cycles of PCR (94° C. for 5 m; followed by 38 cycles of 94° C. for 30 s, 65° C. for 45 s, 72° C. for 60 s; ending with 72° C. for 7 m) using Klentaq. This was sequenced using m13F and m13R as primers. Sequence corresponding to the human pgp was obtained, which corresponded to human pgp 670–1638.

Clone 88/U 750

Nucleobond RNA Maxi kit from Clontech was used according to the manufacturer's instructions to prepare total RNA from Cynomologous monkey liver. Using the SMART Race cDNA Amplification Kit from Clontech, first strand cDNA was prepared from this RNA. The Universal Primer provided with this kit and the gene specific primer, ps088 were used with this template for 40 cycles of Touchdown PCR (94° C. for 5 m; followed by 5 cycles of 94° C. for 30 s, 72° C. for 120 s, 94° C. for 30 s; 5 cycles of 94° C. for 30 s, 70° C. for 45 s, 72° C. for 120 s; 30 cycles of 94° C. for 30 s, 68° C. for 45 s, 72° C. for 120 s; ending with 72° C. for 7 m) using Advantage 2 Taq. A 750 nucleotide fragment was obtained and sequenced with m13F and m13R primers. This represented the 5' end of the cDNA including the start codon. It showed good homology to the human sequence from 275–775 (the start codon for the human sequence being at 433).

Assembly of Complete cDNA

Clone AB

Clone 88/U 750 was digested with NaeI/SacI. A 339 nucleotide fragment was isolated on a gel, and purified using the Qiaquick Gel Extraction Kit (Qiagen) according to the manufacturer's instructions. Clone 70/78C was digested with SacI/EcoRI, a 916 nucleotide fragment was isolated on a gel, and purified using the Qiaquick Gel Extraction Kit (Qiagen) according to the manufacturer's instructions. These were ligated together into pUC 19 SmaI/EcorRI/SAP.

Clone CD

Clone 72/73 was digested with EcoRI/KpnI. A 1.6 kb fragment was isolated on a gel, and purified using the Qiaquick Gel Extraction Kit (Qiagen) according to the manufacturer's instructions. Clone 79/77 C1500 was digested with KpnI/DraI. A 1.1 kb fragment was isolated on a gel, and purified using the Qiaquick Gel Extraction Kit (Qiagen) according to the manufacturer's instructions. These were ligated into pUC 19 EcoRI/SmaI/SAP.

Complete cDNA

Clone AB was digested with Hinc II/EcoRI. A 1.3 kb fragment was isolated on a gel, and purified using the Qiaquick Gel Extraction Kit (Qiagen) according to the manufacturer's instructions.

Clone CD was digested with EcoRI/Ehel. The 5.2 kb fragment was isolated on a gel, and purified using the Qiaquick Gel Extraction Kit (Qiagen) according to the manufacturer's instructions.

These were ligated together, transformed into SCS-1 Competent Cells (Stratagene) according to the manufacturer's instructions. Promising clones were identified by restriction digest. The identity of the final clone was confirmed by sequencing.

The nucleotide sequence of the cynomologous P-glycoprotein is presented as SEQ ID NO:1. The coding sequence consists of nucleotides 100–3940, producing a polypeptide of 1280 amino acids (SEQ ID NO:2).

Sequencing of additional clones from libraries of individual cynomologous monkeys indicated the presence of a polymorphism comprising an unexpected 9 base pair insert in the cDNA that is also present in the genomic sequence from the same individual monkey. The polymorphism resulted in an insertion of three amino acids after amino acid 92. The nucleotide sequence of this allelic variant is presented as SEQ ID NO:3. The coding sequence consists of nucleotides 100–3949, producing a polypeptide of 1283 amino acids (SEQ ID NO:4). The cynomologous PGP cDNA (SEQ ID NO:3) cloned in plasmid pUCI9 was deposited with ATCC (deposit number PTA-809).

EXAMPLE 2

Activity of Cynomologous P-glycoprotein

Materials and Methods

Cynomologous monkey PGP cDNA (SEQ ID NO:3) is introduced into a clonal population of LLC-PK 1 cells in a vector that confers resistance to hygromycin B. LLC-PK1 cells are obtained from the American Type Culture Collections and are propagated in Medium 199 supplemented to 7% with fetal bovine serum. LLC-PK1 cells are recloned prior to transfection in order to assure homogeneity of the cell population. Briefly, cynomologous monkey PGP cDNA is incorporated into the p222CMV vector. This vector is derived from the p220.2 episomal vector system based on the OriP sequences for Epstein Barr virus and the EBNA-1 gene product (Sugden et al., *Mol. Cell Biol.* 5:410–413, 1985; Yates et al., *Nature* (*Lond.*) 313: 812–815, 1985). The PGP cDNA is under the control of the cytomegalovirus (CMV) immediate early promoter. The vector confers resistance to hygromycin B. Cells (in 0.4 mL) and DNA (10 to 20 $\mu$g) were transfected by electroporation using a BTX Electro cell manipulator model 600 using a 2 mm gap cell, 100V, 2500 $\mu$F capacitance and 72 ohm resistance. After electroporation, the cells are plated in multiwell plates (48 well, Corning Costar) at 10% of confluence. One to two days after transfection hygromycin B is introduced at a final concentration of 400 to 600 $\mu$g/ml. Cells are refed every 2 to 4 days and are propagated in 400 to 600 $\mu$g/ml hygromycin B for 6 to 8 days at which point the bulk of the wild type cells are detached. The hygromycin B is reduced to 100 $\mu$g/ml and maintained in this concentration of hygromycin B. After 14 to 18 days the wells are inspected and wells containing single colonies are trypsinized and scaled up to bulk cultures. Expression of PGP is measured by the polarization of vinblastine (0.1 $\mu$M) transport in Transwells™.

LLC-PK1 cell based transport studies are conducted in 24 well Transwells™(Corning Costar, Catalog number 3415). Transwells™ are prepared by the addition of 0.6 mL media to the basolateral space and 0.1 mL media to the apical space. Cells are seeded at 4×10⁴ cells per insert (typically in 0.05 mL to 0.15 mL), refed with fresh media every 2 to 4 days and used for transport studies 4 to 8 days post seeding. Transport assays are conducted in Hank's balanced saline (HBSS) buffered with 10 mM HEPES (pH 7 to 7.2). Cell monolayers are rinsed with HBSS prior to use in transport assays. Transport is measured under sink conditions in both the apical to basolateral (A to B) and basolateral to apical (B to A) directions. At least duplicate monolayers are used per determination. At the desired time points, samples are withdrawn from the receiver chamber (apical or basolateral chambers). Quantitation of the amount of compound transported is by liquid scintillation counting (vinblastine) or HPLC with UV or mass spectrometric detection.

Cynomologous PGP cDNA is expressed in insect cells using a baculovirus vector. Membranes are prepared according to the method of (Sarkadi et al., *J. Biol. Chem.* 267: 4854–4858, 1992) and stored at −80° C. until use. ATPase assays are conducted in 96 well microtiter plates. The assays are conducted using a modification of the methods of (Sarkadi et al., 1992 and Druekes et al., *Anal. Biochem.* 230: 173–177, 1995).

A detailed method for each well of a 96 well plate is contained below: A 0.06 ml reaction mixture containing 40 $\mu$g membranes, 20 $\mu$M Verapamil (positive control) or test drug, and 3–5 mM MgATP, in buffer containing 50 mM Tris-MES, 2 mM EGTA, 50 mM KCl, 2 mM dithiothreitol, and 5 mM sodium azide, is incubated at 37° C. for 20 min. An identical reaction mixture containing 100 $\mu$M sodium orthovanadate is assayed in pallel. Orthovanadate inhibits PGP by trapping MgADP in the nucleotide binding site. Thus, ATPase activity measured in the presence of orthovanadate represents non-PGP ATPase activity and can be subtracted from the activity generated without orthovanadate to yield vanadate-sensitive ATPase activity. The reaction is stopped by the addition of 30 $\mu$l of 10% SDS + Antifoam A. Two additional reaction mixtures (+and − orthovanadate) but without MgATP, are also prepared and incubated with the others, and then supplemented with SDS and MgATP, to represent time=0 min of reaction. The incubations are followed with addition of 200 $\mu$l of 35 mM ammonium molybdate in 15 mM zinc acetate:10% ascorbic acid (1:4) and incubated for an additional 20 min at 37° C. The liberation of inorganic phosphate is detected by its absorbance at 800 nm and quantitated by comparing the absorbance to a phosphate standard curve.

Ligand binding assays and assays for measuring inhibition of fluorescent dye uptake are preformed as described by Sharom et al. (*Biochem. Pharmacol.* 58:571–586, 1999).

1. Stable PGP Expression in LLC-PK1 Cells.

Functional expression of cynomologous monkey PGP is measured by the polarization of transport of vinblastine. Control cells typically demonstrate a B to A/A to B ratio of between 1 and 3. PGP transfected cells demonstrate a much higher ratio. The expression of cDNA-derived cynomologous monkey is stable.

II. Activation of ATPase Activity in PGP Membranes.

The stimulation of ATPase assay provides a rapid measure of the concentration dependence of any interaction of a drug with PGP. The liberated inorganic phosphate is measured by a simple spectrophotometric assay performed in a microtiter plate format. The testing of multiple drug concentrations allows estimation of the affinity of the drug for PGP and whether saturation of the response was observed.

III. Drug Transport Across Cell Monolayers.

The ATPase assay does not directly measure drug transport. In order to examine the concordance between activation of ATPase and actual transport, the rates of transport of the drugs are measured in control LLC-PK1 and cynomologous monkey PGP cell monolayers. For each drug concentration, four measurements are made:

| A: | A to B | Control cells |
| B: | B to A | Control cells |
| C: | A to B | PGP cells |
| D: | B to A | PGP cells |

The polarization of transport is calculated in control cells (B/A) and PGP cells (D/C). The intrinsic activity (IA) of PGP is calculated as the sum of the amount PGP facilitated B to A transport in PGP cells relative to control cells (D minus B) and the amount that PGP impeded A to B transport in PGP cells relative to control cells (A minus C). The intrinsic clearance of PGP is calculated from a plot of the concentration dependence data by either calculating the slope of the line under non-saturating conditions or from the calculated apparent Km and Vmax values when saturation is observed. Intrinsic clearance is expressed as $mL/m^2/min$.

The ATPase data provides useful concentration response data. For example, the apparent Km values for some compounds are in good agreement between the ATPase and transport systems. However, other drugs activate ATPase activity but transport by PGP is not detectable. At the least, ATPase assay can identify a concentration range below which the response to transport by PGP was linear with respect to drug concentration. This should allow simplification of the experimental design for measuring the intrinsic clearance of PGP, an important consideration if large numbers of compounds are to be tested.

IV. Bioavailability

Bioavailability studies are performed by performing one or more of the assays described above with two or more different PGP types. The different PGP types can by different species (e.g., dog and human, cynomologous monkey and human, dog and cynomologous monkey, etc.) or can be different alleles of the same species. The results of these assays are compared to determine or estimate the bioavailability of a drug in individuals of the different species or in individuals that express different PGP alleles. The results of one determination also may be compared to a previously determined value of, e.g., ATPase or transport, as an historical control.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

---

What is claimed is:

1. An isolated nucleic acid molecule selected from the group consisting of
   (a) nucleic acid molecules that code for the amino acid sequence of SEQ ID NO:2 or SEQ ID NO:4,
   (b) variants of the nucleic acid molecules of (a) that encodes a P-glycoprotein having multidrug transport activity and an amino acid sequence that varies from SEQ ID NO:2 or SEQ ID NO:4 by 1, 2, 3, 4 or 5 amino acid, and
   (c) complements of (a) or (b).

2. The isolated nucleic acid molecule of claim 1, wherein the isolated nucleic acid molecule codes for SEQ ID NO:2.

3. The isolated nucleic acid molecule of claim 1, wherein the isolated nucleic acid molecule codes for SEQ ID NO:4.

4. The isolated nucleic molecule of claim 1, wherein he isolated nucleic acid molecule comprises the nucleotide sequence of SEQ ID NO:1 or SEQ ID NO:3.

5. An expression vector comprising the isolated nucleic acid molecule of claim 1 operably linked to a promoter.

6. A host cell transformed or transfected with the expression vector of claim 5.

7. The isolated nucleic acid molecule of claim 2, wherein the isolated nucleic acid molecule comprises nucleotides 100–3940 of SEQ ID NO:1.

8. The isolated nucleic acid molecule of claim 3, wherein the isolated nucleic acid molecule comprises nucleotides 100–3949 of SEQ ID NO:3.

9. An expression vector comprising the isolated nucleic acid molecule of claim 2 operably linked to a promoter.

10. A host cell transformed or transfected with the expression vector of claim 9.

11. An expression vector comprising the isolated nucleic acid molecule of claim 3 operably linked to a promoter.

12. A host cell transformed or transfected with the expression vector of claim 11.

13. An expression vector comprising the isolated nucleic acid molecule of claim 4 operably linked to a promoter.

14. A host cell transformed or transfected with the expression vector of claim 13.

15. An expression vector comprising the isolated nucleic acid molecule of claim 7 operably linked to a promoter.

16. A host cell transformed or transfected with the expression vector of claim 15.

17. An expression vector comprising the isolated nucleic acid molecule of claim 8 operably linked to a promoter.

18. A host cell transformed or transfected with the expression vector of claim 17.

* * * * *

UNITED STATES PATENT AND TRADEMARK OFFICE
CERTIFICATE OF CORRECTION

PATENT NO. : 6,617,450 B1
DATED : September 9, 2003
INVENTOR(S) : Penny J. Stocker et al.

It is certified that error appears in the above-identified patent and that said Letters Patent is hereby corrected as shown below:

<u>Column 85,</u>
Line 42, replace "he" with -- the --.

Signed and Sealed this

Eleventh Day of November, 2003

JAMES E. ROGAN
*Director of the United States Patent and Trademark Office*

SEQUENCE LISTING

```
<160> NUMBER OF SEQ ID NOS:  18

<210> SEQ ID NO 1
<211> LENGTH: 4186
<212> TYPE: DNA
<213> ORGANISM: Macaca fascicularis
<220> FEATURE:
<221> NAME/KEY: CDS
<222> LOCATION: (100)...(3940)

<400> SEQUENCE: 1
ggccgctgtt cgtttccgct aggtctttcc actaaagtcg gagtatcttc ttccaaaatt         60
tcacgacttg gtggccgttc caaggagcgc gaggtcggg atg gat ctt gaa ggg          114
                                            Met Asp Leu Glu Gly
                                              1               5 gac cgc aat gga gga gca gag aag aag aac ttt ttt aaa ctg aac aat         162
Asp Arg Asn Gly Gly Ala Glu Lys Lys Asn Phe Phe Lys Leu Asn Asn
                10                  15                  20 aaa agt aaa aaa gat aag aag gaa agg aaa cca act gtc agt gta ttt         210
Lys Ser Lys Lys Asp Lys Lys Glu Arg Lys Pro Thr Val Ser Val Phe
            25                  30                  35 tca atg ttt cgc tat tca aat tgg ctt gac aag ttg tat atg gtg gtg         258
Ser Met Phe Arg Tyr Ser Asn Trp Leu Asp Lys Leu Tyr Met Val Val
        40                  45                  50 gga act ttg gct gcc atc atc cat gga gct gga ctt cct ctc atg atg         306
Gly Thr Leu Ala Ala Ile Ile His Gly Ala Gly Leu Pro Leu Met Met
    55                  60                  65 ctg gtg ttt gga gac atg acg gat acc ttt gca aat gca gga aat tta         354
Leu Val Phe Gly Asp Met Thr Asp Thr Phe Ala Asn Ala Gly Asn Leu
70                  75                  80                  85 gga gat tta gga gct ctg ttg act aat agc agt aat atc act gat aca         402
```

```
Gly Asp Leu Gly Ala Leu Leu Thr Asn Ser Ser Asn Ile Thr Asp Thr
                90                  95                 100 gtg ccc gtc atg aat ctg gag gaa gat atg acc agg tat gcc tat tat        450
Val Pro Val Met Asn Leu Glu Glu Asp Met Thr Arg Tyr Ala Tyr Tyr
            105                 110                 115 tac agt gga att ggt gct ggg gtg ctg gtt gct gct tac att cag gtt        498
Tyr Ser Gly Ile Gly Ala Gly Val Leu Val Ala Ala Tyr Ile Gln Val
        120                 125                 130 tca ttt tgg tgc ctg gca gct gga aga caa ata cac aaa att aga aaa        546
Ser Phe Trp Cys Leu Ala Ala Gly Arg Gln Ile His Lys Ile Arg Lys
    135                 140                 145 cag ttt ttt cat gct ata atg cga cag gag ata ggc tgg ttt gat gtg        594
Gln Phe Phe His Ala Ile Met Arg Gln Glu Ile Gly Trp Phe Asp Val
150                 155                 160                 165 cac gat gtt ggg gag ctt aac acc cgg ctt aca gat gat gtc tcc aag        642
His Asp Val Gly Glu Leu Asn Thr Arg Leu Thr Asp Asp Val Ser Lys
                170                 175                 180 att aat gaa gga att ggt gac aaa att gga atg ttc ttt cag tca atg        690
Ile Asn Glu Gly Ile Gly Asp Lys Ile Gly Met Phe Phe Gln Ser Met
            185                 190                 195 gca aca ttt ttc act ggg ttt ata gta gga ttt aca cgt ggt tgg aag        738
Ala Thr Phe Phe Thr Gly Phe Ile Val Gly Phe Thr Arg Gly Trp Lys
        200                 205                 210 cta acc ctt gtg att ttg gcc atc agt cct gtt ctt gga ctg tca gct        786
Leu Thr Leu Val Ile Leu Ala Ile Ser Pro Val Leu Gly Leu Ser Ala
    215                 220                 225 gca gtc tgg gca aag ata ctg tct tca ttt act gat aaa gaa ctc tta        834
Ala Val Trp Ala Lys Ile Leu Ser Ser Phe Thr Asp Lys Glu Leu Leu
230                 235                 240                 245 gct tat gca aaa gct gga gca gta gct gaa gag gtc ttg gca gca att        882
Ala Tyr Ala Lys Ala Gly Ala Val Ala Glu Glu Val Leu Ala Ala Ile
                250                 255                 260 aga act gtg att gca ttt gga gga caa aag aaa gaa ctc gaa agg tac        930
Arg Thr Val Ile Ala Phe Gly Gly Gln Lys Lys Glu Leu Glu Arg Tyr
            265                 270                 275 aac aaa aat tta gaa gaa gct aaa aga att ggg ata aag aaa gct att        978
Asn Lys Asn Leu Glu Glu Ala Lys Arg Ile Gly Ile Lys Lys Ala Ile
        280                 285                 290 aca gcc aat att tct ata ggt gct gct ttc ctg ctt atc tat gca tct       1026
Thr Ala Asn Ile Ser Ile Gly Ala Ala Phe Leu Leu Ile Tyr Ala Ser
    295                 300                 305 tat gct ctg gcc ttc tgg tat ggg acc acc ttg gtc ctc tca aag gaa       1074
Tyr Ala Leu Ala Phe Trp Tyr Gly Thr Thr Leu Val Leu Ser Lys Glu
310                 315                 320                 325 tat tct att gga caa gta ctc act gta ttc ttt tct gta tta att ggg       1122
Tyr Ser Ile Gly Gln Val Leu Thr Val Phe Phe Ser Val Leu Ile Gly
                330                 335                 340 gct ttt agt gtt gga cag gca tct cca agc att gaa gca ttt gca aat       1170
Ala Phe Ser Val Gly Gln Ala Ser Pro Ser Ile Glu Ala Phe Ala Asn
            345                 350                 355 gca aga gga gca gct ttt gaa atc ttc aag ata att gat aat aag cca       1218
Ala Arg Gly Ala Ala Phe Glu Ile Phe Lys Ile Ile Asp Asn Lys Pro
        360                 365                 370 agt att gac agc tat tcg aag agt ggg cac aaa cca gat aat att aag       1266
Ser Ile Asp Ser Tyr Ser Lys Ser Gly His Lys Pro Asp Asn Ile Lys
    375                 380                 385 gga aat ttg gaa ttc aga aat gtt cac ttc agt tac cca tct cga aaa       1314
Gly Asn Leu Glu Phe Arg Asn Val His Phe Ser Tyr Pro Ser Arg Lys
390                 395                 400                 405
```

-continued

```
gaa gtt aag atc ttg aag ggc ctg aac ctg aag gtg cag agt ggg cag    1362
Glu Val Lys Ile Leu Lys Gly Leu Asn Leu Lys Val Gln Ser Gly Gln
            410                 415                 420 acg gtg gcc ctg gtt gga aac agc ggc tgt ggg aag agc aca acg gtc    1410
Thr Val Ala Leu Val Gly Asn Ser Gly Cys Gly Lys Ser Thr Thr Val
        425                 430                 435 cag ctg atg cag agg ctt tat gac ccc aca gag ggc atg gtc agt gtt    1458
Gln Leu Met Gln Arg Leu Tyr Asp Pro Thr Glu Gly Met Val Ser Val
    440                 445                 450 gat gga cag gat att agg acc ata aac gta agg ttt cta cgg gaa atc    1506
Asp Gly Gln Asp Ile Arg Thr Ile Asn Val Arg Phe Leu Arg Glu Ile
455                 460                 465 atc ggt gtg gtg agt cag gaa cct gta ttg ttt gcc acc acg ata gct    1554
Ile Gly Val Val Ser Gln Glu Pro Val Leu Phe Ala Thr Thr Ile Ala
470                 475                 480                 485 gaa aac att cgc tat ggt cgt gaa gat gtc acc atg gat gag att gag    1602
Glu Asn Ile Arg Tyr Gly Arg Glu Asp Val Thr Met Asp Glu Ile Glu
            490                 495                 500 aaa gct gtc aag gaa gcc aat gcc tat gac ttt atc atg aaa ctg cct    1650
Lys Ala Val Lys Glu Ala Asn Ala Tyr Asp Phe Ile Met Lys Leu Pro
        505                 510                 515 cag aaa ttt gac acc ctg gtt gga gag aga ggg gcc cag ctg agt ggt    1698
Gln Lys Phe Asp Thr Leu Val Gly Glu Arg Gly Ala Gln Leu Ser Gly
    520                 525                 530 ggg cag aag cag agg atc gcc att gca cgt gcc ctg gtt cgc aac ccc    1746
Gly Gln Lys Gln Arg Ile Ala Ile Ala Arg Ala Leu Val Arg Asn Pro
535                 540                 545 aag atc ctc ctg ctg gac gag gcc acg tca gcc ttg gac aca gaa agt    1794
Lys Ile Leu Leu Leu Asp Glu Ala Thr Ser Ala Leu Asp Thr Glu Ser
550                 555                 560                 565 gaa gca gtg gtt cag gtg gct ctg gat aag gcc aga aaa ggt cgg acc    1842
Glu Ala Val Val Gln Val Ala Leu Asp Lys Ala Arg Lys Gly Arg Thr
            570                 575                 580 acc att gtg ata gct cat cgt ttg tct acg gtt cgt aat gcc gac gtc    1890
Thr Ile Val Ile Ala His Arg Leu Ser Thr Val Arg Asn Ala Asp Val
        585                 590                 595 atc gct ggt ttc gat gat gga gtc att gtg gag aaa gga aat cat gat    1938
Ile Ala Gly Phe Asp Asp Gly Val Ile Val Glu Lys Gly Asn His Asp
    600                 605                 610 gag ctc atg aaa gag aaa ggc att tac ttc aaa ctt gtc aca atg cag    1986
Glu Leu Met Lys Glu Lys Gly Ile Tyr Phe Lys Leu Val Thr Met Gln
615                 620                 625 aca gca gga aat gaa att gaa tta gaa aat gca gct gat gaa tcc aaa    2034
Thr Ala Gly Asn Glu Ile Glu Leu Glu Asn Ala Ala Asp Glu Ser Lys
630                 635                 640                 645 agt gaa att gat acc ttg gaa atg tct tca cat gat tca gga tcc agt    2082
Ser Glu Ile Asp Thr Leu Glu Met Ser Ser His Asp Ser Gly Ser Ser
            650                 655                 660 cta ata aga aaa aga tcc act cgt agg agt gtc cgt gga tca caa ggc    2130
Leu Ile Arg Lys Arg Ser Thr Arg Arg Ser Val Arg Gly Ser Gln Gly
        665                 670                 675 caa gac aga aag ctt agt acc aaa gag gct ctg gat gaa agt ata cct    2178
Gln Asp Arg Lys Leu Ser Thr Lys Glu Ala Leu Asp Glu Ser Ile Pro
    680                 685                 690 cca gtt tcc ttt tgg agg att atg aag cta aat tta act gag tgg cct    2226
Pro Val Ser Phe Trp Arg Ile Met Lys Leu Asn Leu Thr Glu Trp Pro
695                 700                 705 tat ttt gtt gtt ggt gta ttt tgt gcc att ata aat gga ggt ctg caa    2274
Tyr Phe Val Val Gly Val Phe Cys Ala Ile Ile Asn Gly Gly Leu Gln
            710                 715                 720                 725
```

-continued

| | |
|---|---|
| cca gca ttt gca gta ata ttt tca aag att ata ggg att ttt aca aga<br>Pro Ala Phe Ala Val Ile Phe Ser Lys Ile Ile Gly Ile Phe Thr Arg<br>730           735           740 | 2322 |
| aat gat gat gcc gaa aca aaa cga cag aat agt aac ttg ttt tca cta<br>Asn Asp Asp Ala Glu Thr Lys Arg Gln Asn Ser Asn Leu Phe Ser Leu<br>745           750           755 | 2370 |
| ttg ttt cta gtc ctt gga att gtt tct ttt att aca ttt ttc ctt cag<br>Leu Phe Leu Val Leu Gly Ile Val Ser Phe Ile Thr Phe Phe Leu Gln<br>760           765           770 | 2418 |
| ggc ttc aca ttt ggc aaa gct gga gag atc ctc acc aag cgg ctc cga<br>Gly Phe Thr Phe Gly Lys Ala Gly Glu Ile Leu Thr Lys Arg Leu Arg<br>775           780           785 | 2466 |
| tac atg gtt ttc cga tcc atg ctc aga cag gat gtg agc tgg ttt gat<br>Tyr Met Val Phe Arg Ser Met Leu Arg Gln Asp Val Ser Trp Phe Asp<br>790           795           800           805 | 2514 |
| gac cct aaa aac acc act gga gca ttg act acc agg ctc gcc aat gat<br>Asp Pro Lys Asn Thr Thr Gly Ala Leu Thr Thr Arg Leu Ala Asn Asp<br>810           815           820 | 2562 |
| gct gct caa gtt aaa ggg gct ata ggt tcc agg ctt gct ata att acc<br>Ala Ala Gln Val Lys Gly Ala Ile Gly Ser Arg Leu Ala Ile Ile Thr<br>825           830           835 | 2610 |
| cag aat ata gca aat ctt ggg aca gga ata att ata tcc tta atc tat<br>Gln Asn Ile Ala Asn Leu Gly Thr Gly Ile Ile Ile Ser Leu Ile Tyr<br>840           845           850 | 2658 |
| ggt tgg caa ctg aca ctg tta ctc tta gca att gta ccc atc att gca<br>Gly Trp Gln Leu Thr Leu Leu Leu Ala Ile Val Pro Ile Ile Ala<br>855           860           865 | 2706 |
| ata gca gga gtt gtt gaa atg aaa atg ttg tct gga caa gca ctg aaa<br>Ile Ala Gly Val Val Glu Met Lys Met Leu Ser Gly Gln Ala Leu Lys<br>870           875           880           885 | 2754 |
| gat aag aaa gaa cta gaa ggt gct ggg aag atc gct act gaa gca ata<br>Asp Lys Lys Glu Leu Glu Gly Ala Gly Lys Ile Ala Thr Glu Ala Ile<br>890           895           900 | 2802 |
| gaa aac ttc cga act gtt gtt tct ttg act cag gag cag aag ttt gaa<br>Glu Asn Phe Arg Thr Val Val Ser Leu Thr Gln Glu Gln Lys Phe Glu<br>905           910           915 | 2850 |
| cat atg tat gat cag agt ttg cag gta cca tac aga aac tct ttg agg<br>His Met Tyr Asp Gln Ser Leu Gln Val Pro Tyr Arg Asn Ser Leu Arg<br>920           925           930 | 2898 |
| aaa gca cac atc ttt gga atc acg ttt tcc ttc acg cag gca atg atg<br>Lys Ala His Ile Phe Gly Ile Thr Phe Ser Phe Thr Gln Ala Met Met<br>935           940           945 | 2946 |
| tat ttt tcc tat gct gga tgt ttc cgg ttt gga gcc tac ttg gtg gca<br>Tyr Phe Ser Tyr Ala Gly Cys Phe Arg Phe Gly Ala Tyr Leu Val Ala<br>950           955           960           965 | 2994 |
| cat agt ctc atg agc ttt gag gat gtt ctg tta gta ttt tca gct gtt<br>His Ser Leu Met Ser Phe Glu Asp Val Leu Leu Val Phe Ser Ala Val<br>970           975           980 | 3042 |
| gtc ttt ggt gcc atg gcc gtg ggg caa gtc agt tca ttt gct cct gac<br>Val Phe Gly Ala Met Ala Val Gly Gln Val Ser Ser Phe Ala Pro Asp<br>985           990           995 | 3090 |
| tat gcc aaa gcc aaa gta tca gca gcc cac atc atc atg atc att gaa<br>Tyr Ala Lys Ala Lys Val Ser Ala Ala His Ile Ile Met Ile Ile Glu<br>1000          1005          1010 | 3138 |
| aaa acc cct ttg att gac agc tac agc aca gaa ggc cta aag ccg aac<br>Lys Thr Pro Leu Ile Asp Ser Tyr Ser Thr Glu Gly Leu Lys Pro Asn<br>1015          1020          1025 | 3186 |
| aca ttg gaa gga aat gtc aca ttt aat gaa gtt gta ttc aac tat ccc<br>Thr Leu Glu Gly Asn Val Thr Phe Asn Glu Val Val Phe Asn Tyr Pro | 3234 |

```
                                                                -continued
       1030           1035           1040           1045 acc cga ctg gac atc cca gtg ctt cag ggg ctg agc ctg gaa gtg aag        3282
Thr Arg Leu Asp Ile Pro Val Leu Gln Gly Leu Ser Leu Glu Val Lys
            1050               1055               1060 aag ggc cag acg ctg gcc ctg gtg ggc agc agt ggc tgt ggg aag agc        3330
Lys Gly Gln Thr Leu Ala Leu Val Gly Ser Ser Gly Cys Gly Lys Ser
            1065               1070               1075 acg gtg gtc cag ctc ctg gag cgg ttc tat gac ccc ttg gcg ggg aaa        3378
Thr Val Val Gln Leu Leu Glu Arg Phe Tyr Asp Pro Leu Ala Gly Lys
            1080               1085               1090 gtg ctg ctt gac ggc aaa gaa ata aag caa ctg aat gtt cag tgg ctc        3426
Val Leu Leu Asp Gly Lys Glu Ile Lys Gln Leu Asn Val Gln Trp Leu
       1095               1100               1105 cga gca cac ctg ggc atc gtg tcc cag gag ccc atc ctg ttt gac tgc        3474
Arg Ala His Leu Gly Ile Val Ser Gln Glu Pro Ile Leu Phe Asp Cys
1110               1115               1120               1125 agc att agt gag aac att gcc tat gga gac aac agc cgg gtg gtg tca        3522
Ser Ile Ser Glu Asn Ile Ala Tyr Gly Asp Asn Ser Arg Val Val Ser
                1130               1135               1140 cag gaa gag atc gtg agg gca gcc aag gag gcc aat ata cac gcc ttc        3570
Gln Glu Glu Ile Val Arg Ala Ala Lys Glu Ala Asn Ile His Ala Phe
                1145               1150               1155 atc gag tca ctg cct aat aaa tat agc acc aga gta gga gac aaa gga        3618
Ile Glu Ser Leu Pro Asn Lys Tyr Ser Thr Arg Val Gly Asp Lys Gly
            1160               1165               1170 act cag ctc tct ggt ggc cag aaa caa cgc att gcc ata gct cgt gcc        3666
Thr Gln Leu Ser Gly Gly Gln Lys Gln Arg Ile Ala Ile Ala Arg Ala
       1175               1180               1185 ctt gtt aga cag cct cat att ttg ctt ttg gat gaa gcc aca tca gct        3714
Leu Val Arg Gln Pro His Ile Leu Leu Leu Asp Glu Ala Thr Ser Ala
1190               1195               1200               1205 ctg gat aca gaa agt gaa aag gtt gtc caa gaa gcc ctg gac aaa gcc        3762
Leu Asp Thr Glu Ser Glu Lys Val Val Gln Glu Ala Leu Asp Lys Ala
                1210               1215               1220 aga gaa ggc cgt acc tgc att gtg att gct cac cgc ctg tcc acc atc        3810
Arg Glu Gly Arg Thr Cys Ile Val Ile Ala His Arg Leu Ser Thr Ile
                1225               1230               1235 cag aat gca gac tta ata gtg gtg ttt cag aat ggc aga gtc aag gag        3858
Gln Asn Ala Asp Leu Ile Val Val Phe Gln Asn Gly Arg Val Lys Glu
            1240               1245               1250 cac ggc aca cat cag cag ctg ctg gca cag aaa ggc atc tat ttt tca        3906
His Gly Thr His Gln Gln Leu Leu Ala Gln Lys Gly Ile Tyr Phe Ser
       1255               1260               1265 atg gtc agt gtc cag gct gga gca aag cgc cag t gaactgtgac                3950
Met Val Ser Val Gln Ala Gly Ala Lys Arg Gln
1270               1275               1280 tgtatgagat gttaaatatt ttttaatatt tgtgtttaaa tatggcattt attcaaagtt      4010
aaaaagcaag tacttataga attatgaaga gttatctgtt taacatttcc tcaaccaagt      4070
tcagagtctt cagacactcg taattaaagg aagagagcga gagacatcat caagtggaga      4130
gaaataatgg tttaaattgc attataaatt ttataacaga gttaaagtag atttt           4186

<210> SEQ ID NO 2
<211> LENGTH: 1280
<212> TYPE: PRT
<213> ORGANISM: Macaca fascicularis

<400> SEQUENCE: 2

Met Asp Leu Glu Gly Asp Arg Asn Gly Gly Ala Glu Lys Lys Asn Phe
```

-continued

```
  1               5                    10                   15
Phe Lys Leu Asn Asn Lys Ser Lys Lys Asp Lys Lys Glu Arg Lys Pro
                 20                  25                  30

Thr Val Ser Val Phe Ser Met Phe Arg Tyr Ser Asn Trp Leu Asp Lys
             35                  40                  45

Leu Tyr Met Val Val Gly Thr Leu Ala Ala Ile Ile His Gly Ala Gly
 50                          55                  60

Leu Pro Leu Met Met Leu Val Phe Gly Asp Met Thr Asp Thr Phe Ala
 65                  70                  75                  80

Asn Ala Gly Asn Leu Gly Asp Leu Gly Ala Leu Leu Thr Asn Ser Ser
                 85                  90                  95

Asn Ile Thr Asp Thr Val Pro Val Met Asn Leu Glu Glu Asp Met Thr
             100                 105                 110

Arg Tyr Ala Tyr Tyr Ser Gly Ile Gly Ala Gly Val Leu Val Ala
             115                 120                 125

Ala Tyr Ile Gln Val Ser Phe Trp Cys Leu Ala Ala Gly Arg Gln Ile
 130                 135                 140

His Lys Ile Arg Lys Gln Phe His Ala Ile Met Arg Gln Glu Ile
 145                 150                 155                 160

Gly Trp Phe Asp Val His Asp Val Gly Glu Leu Asn Thr Arg Leu Thr
                 165                 170                 175

Asp Asp Val Ser Lys Ile Asn Glu Gly Ile Gly Asp Lys Ile Gly Met
             180                 185                 190

Phe Phe Gln Ser Met Ala Thr Phe Phe Thr Gly Phe Ile Val Gly Phe
             195                 200                 205

Thr Arg Gly Trp Lys Leu Thr Leu Val Ile Leu Ala Ile Ser Pro Val
 210                 215                 220

Leu Gly Leu Ser Ala Ala Val Trp Ala Lys Ile Leu Ser Ser Phe Thr
 225                 230                 235                 240

Asp Lys Glu Leu Leu Ala Tyr Ala Lys Ala Gly Ala Val Ala Glu Glu
                 245                 250                 255

Val Leu Ala Ala Ile Arg Thr Val Ile Ala Phe Gly Gly Gln Lys Lys
             260                 265                 270

Glu Leu Glu Arg Tyr Asn Lys Asn Leu Glu Glu Ala Lys Arg Ile Gly
             275                 280                 285

Ile Lys Lys Ala Ile Thr Ala Asn Ile Ser Ile Gly Ala Ala Phe Leu
 290                 295                 300

Leu Ile Tyr Ala Ser Tyr Ala Leu Ala Phe Trp Tyr Gly Thr Thr Leu
 305                 310                 315                 320

Val Leu Ser Lys Glu Tyr Ser Ile Gly Gln Val Leu Thr Val Phe Phe
                 325                 330                 335

Ser Val Leu Ile Gly Ala Phe Ser Val Gly Gln Ala Ser Pro Ser Ile
             340                 345                 350

Glu Ala Phe Ala Asn Ala Arg Gly Ala Ala Phe Glu Ile Phe Lys Ile
             355                 360                 365

Ile Asp Asn Lys Pro Ser Ile Asp Ser Tyr Ser Lys Ser Gly His Lys
 370                 375                 380

Pro Asp Asn Ile Lys Gly Asn Leu Glu Phe Arg Asn Val His Phe Ser
 385                 390                 395                 400

Tyr Pro Ser Arg Lys Glu Val Lys Ile Leu Lys Gly Leu Asn Leu Lys
                 405                 410                 415

Val Gln Ser Gly Gln Thr Val Ala Leu Val Gly Asn Ser Gly Cys Gly
             420                 425                 430
```

-continued

```
Lys Ser Thr Thr Val Gln Leu Met Gln Arg Leu Tyr Asp Pro Thr Glu
        435                 440                 445
Gly Met Val Ser Val Asp Gly Gln Asp Ile Arg Thr Ile Asn Val Arg
450                 455                 460
Phe Leu Arg Glu Ile Ile Gly Val Ser Gln Glu Pro Val Leu Phe
465                 470                 475                 480
Ala Thr Thr Ile Ala Glu Asn Ile Arg Tyr Gly Arg Glu Asp Val Thr
                    485                 490                 495
Met Asp Glu Ile Glu Lys Ala Val Lys Glu Ala Asn Ala Tyr Asp Phe
                500                 505                 510
Ile Met Lys Leu Pro Gln Lys Phe Asp Thr Leu Val Gly Glu Arg Gly
        515                 520                 525
Ala Gln Leu Ser Gly Gly Gln Lys Gln Arg Ile Ala Ile Ala Arg Ala
530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
                580                 585                 590
Arg Asn Ala Asp Val Ile Ala Gly Phe Asp Asp Gly Val Ile Val Glu
                595                 600                 605
Lys Gly Asn His Asp Glu Leu Met Lys Glu Lys Gly Ile Tyr Phe Lys
                610                 615                 620
Leu Val Thr Met Gln Thr Ala Gly Asn Glu Ile Glu Leu Glu Asn Ala
625                 630                 635                 640
Ala Asp Glu Ser Lys Ser Glu Ile Asp Thr Leu Glu Met Ser Ser His
                645                 650                 655
Asp Ser Gly Ser Ser Leu Ile Arg Lys Arg Ser Thr Arg Arg Ser Val
                660                 665                 670
Arg Gly Ser Gln Gly Gln Asp Arg Lys Leu Ser Thr Lys Glu Ala Leu
                675                 680                 685
Asp Glu Ser Ile Pro Pro Val Ser Phe Trp Arg Ile Met Lys Leu Asn
                690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Val Ile Phe Ser Lys Ile Ile
                725                 730                 735
Gly Ile Phe Thr Arg Asn Asp Asp Ala Glu Thr Lys Arg Gln Asn Ser
                740                 745                 750
Asn Leu Phe Ser Leu Leu Phe Leu Val Leu Gly Ile Val Ser Phe Ile
                755                 760                 765
Thr Phe Phe Leu Gln Gly Phe Thr Phe Gly Lys Ala Gly Glu Ile Leu
                770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Ile Ile Thr Gln Asn Ile Ala Asn Leu Gly Thr Gly Ile Ile
                835                 840                 845
```

-continued

Ile Ser Leu Ile Tyr Gly Trp Gln Leu Thr Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Asp Gln Ser Leu Gln Val Pro Tyr
            915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Ser Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Val Ser Ala Ala His Ile
            995                 1000                1005

Ile Met Ile Ile Glu Lys Thr Pro Leu Ile Asp Ser Tyr Ser Thr Glu
    1010                1015                1020

Gly Leu Lys Pro Asn Thr Leu Glu Gly Asn Val Thr Phe Asn Glu Val
1025                1030                1035                1040

Val Phe Asn Tyr Pro Thr Arg Leu Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
            1075                1080                1085

Pro Leu Ala Gly Lys Val Leu Leu Asp Gly Lys Glu Ile Lys Gln Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ser Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Arg
            1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Ala Lys Arg Gln

<210> SEQ ID NO 3
<211> LENGTH: 4195
<212> TYPE: DNA
<213> ORGANISM: Macaca fascicularis
<220> FEATURE:
<221> NAME/KEY: CDS
<222> LOCATION: (100)...(3949)

<400> SEQUENCE: 3

| | |
|---|---:|
| ggccgctgtt cgtttccgct aggtctttcc actaaagtcg gagtatcttc ttccaaaatt | 60 |

| | | |
|---|---|---:|
| tcacgacttg gtggccgttc caaggagcgc gaggtcggg atg gat ctt gaa ggg<br>                                                     Met Asp Leu Glu Gly<br>                                                      1                5 | 114 |

```
gac cgc aat gga gga gca gag aag aag aac ttt ttt aaa ctg aac aat       162
Asp Arg Asn Gly Gly Ala Glu Lys Lys Asn Phe Phe Lys Leu Asn Asn
         10                  15                  20 aaa agt aaa aaa gat aag aag gaa agg aaa cca act gtc agt gta ttt       210
Lys Ser Lys Lys Asp Lys Lys Glu Arg Lys Pro Thr Val Ser Val Phe
     25                  30                  35 tca atg ttt cgc tat tca aat tgg ctt gac aag ttg tat atg gtg gtg       258
Ser Met Phe Arg Tyr Ser Asn Trp Leu Asp Lys Leu Tyr Met Val Val
 40                  45                  50 gga act ttg gct gcc atc atc cat gga gct gga ctt cct ctc atg atg       306
Gly Thr Leu Ala Ala Ile Ile His Gly Ala Gly Leu Pro Leu Met Met
     55                  60                  65 ctg gtg ttt gga gac atg acg gat acc ttt gca aat gca gga aat tta       354
Leu Val Phe Gly Asp Met Thr Asp Thr Phe Ala Asn Ala Gly Asn Leu
 70                  75                  80                  85 gga gat tta gga gct ctg ttg ttt aac aac act aat agc agt aat atc       402
Gly Asp Leu Gly Ala Leu Leu Phe Asn Asn Thr Asn Ser Ser Asn Ile
         90                  95                 100 act gat aca gtg ccc gtc atg aat ctg gag gaa gat atg acc agg tat       450
Thr Asp Thr Val Pro Val Met Asn Leu Glu Glu Asp Met Thr Arg Tyr
        105                 110                 115 gcc tat tat tac agt gga att ggt gct ggg gtg ctg gtt gct gct tac       498
Ala Tyr Tyr Tyr Ser Gly Ile Gly Ala Gly Val Leu Val Ala Ala Tyr
    120                 125                 130 att cag gtt tca ttt tgg tgc ctg gca gct gga aga caa ata cac aaa       546
Ile Gln Val Ser Phe Trp Cys Leu Ala Ala Gly Arg Gln Ile His Lys
135                 140                 145 att aga aaa cag ttt ttt cat gct ata atg cga cag gag ata ggc tgg       594
Ile Arg Lys Gln Phe Phe His Ala Ile Met Arg Gln Glu Ile Gly Trp
150                 155                 160                 165 ttt gat gtg cac gat gtt ggg gag ctt aac acc cgg ctt aca gat gat       642
Phe Asp Val His Asp Val Gly Glu Leu Asn Thr Arg Leu Thr Asp Asp
                170                 175                 180 gtc tcc aag att aat gaa gga att ggt gac aaa att gga atg ttc ttt       690
Val Ser Lys Ile Asn Glu Gly Ile Gly Asp Lys Ile Gly Met Phe Phe
            185                 190                 195 cag tca atg gca aca ttt ttc act ggg ttt ata gta gga ttt aca cgt       738
Gln Ser Met Ala Thr Phe Phe Thr Gly Phe Ile Val Gly Phe Thr Arg
        200                 205                 210 ggt tgg aag cta acc ctt gtg att tgg gcc atc agt cct gtt ctt gga       786
Gly Trp Lys Leu Thr Leu Val Ile Trp Ala Ile Ser Pro Val Leu Gly
    215                 220                 225 ctg tca gct gca gtc tgg gca aag ata ctg tct tca ttt act gat aaa       834
Leu Ser Ala Ala Val Trp Ala Lys Ile Leu Ser Ser Phe Thr Asp Lys
230                 235                 240                 245
```

```
gaa ctc tta gct tat gca aaa gct gga gca gta gct gaa gag gtc ttg      882
Glu Leu Leu Ala Tyr Ala Lys Ala Gly Ala Val Ala Glu Glu Val Leu
            250                 255                 260 gca gca att aga act gtg att gca ttt gga gga caa aag aaa gaa ctc      930
Ala Ala Ile Arg Thr Val Ile Ala Phe Gly Gly Gln Lys Lys Glu Leu
            265                 270                 275 gaa agg tac aac aaa aat tta gaa gaa gct aaa aga att gga ata aag      978
Glu Arg Tyr Asn Lys Asn Leu Glu Glu Ala Lys Arg Ile Gly Ile Lys
            280                 285                 290 aaa gct att aca gcc aat att tct ata ggt gct gct ttc ctg ctt atc     1026
Lys Ala Ile Thr Ala Asn Ile Ser Ile Gly Ala Ala Phe Leu Leu Ile
            295                 300                 305 tat gca tct tat gct ctg gcc ttc tgg tat ggg acc acc ttg gtc ctc     1074
Tyr Ala Ser Tyr Ala Leu Ala Phe Trp Tyr Gly Thr Thr Leu Val Leu
310             315                 320                 325 tca aag gaa tat tct att gga caa gta ctc act gta ttc ttt tct gta     1122
Ser Lys Glu Tyr Ser Ile Gly Gln Val Leu Thr Val Phe Phe Ser Val
            330                 335                 340 tta att ggg gct ttt agt gtt gga cag gca tct cca agc att gaa gca     1170
Leu Ile Gly Ala Phe Ser Val Gly Gln Ala Ser Pro Ser Ile Glu Ala
            345                 350                 355 ttt gca aat gca aga gga gca gct ttt gaa atc ttc aag ata att gat     1218
Phe Ala Asn Ala Arg Gly Ala Ala Phe Glu Ile Phe Lys Ile Ile Asp
            360                 365                 370 aat aag cca agt att gac agc tat tcg aag agt ggg cac aaa cca gat     1266
Asn Lys Pro Ser Ile Asp Ser Tyr Ser Lys Ser Gly His Lys Pro Asp
            375                 380                 385 aat att aag gga aat ttg gaa ttc aga aat gtt cac ttc agt tac cca     1314
Asn Ile Lys Gly Asn Leu Glu Phe Arg Asn Val His Phe Ser Tyr Pro
390             395                 400                 405 tct cga aaa gaa gtt aag atc ttg aag ggc ctg aac ctg aag gtg cag     1362
Ser Arg Lys Glu Val Lys Ile Leu Lys Gly Leu Asn Leu Lys Val Gln
            410                 415                 420 agt ggg cag acg gtg gcc ctg gtt gga aac agc ggc tgt ggg aag agc     1410
Ser Gly Gln Thr Val Ala Leu Val Gly Asn Ser Gly Cys Gly Lys Ser
            425                 430                 435 aca acg gtc cag ctg atg cag agg ctt tat gac ccc aca gag ggc atg     1458
Thr Thr Val Gln Leu Met Gln Arg Leu Tyr Asp Pro Thr Glu Gly Met
            440                 445                 450 gtc agt gtt gat gga cag gat att agg acc ata aac gta agg ttt cta     1506
Val Ser Val Asp Gly Gln Asp Ile Arg Thr Ile Asn Val Arg Phe Leu
455             460                 465 cgg gaa atc atc ggt gtg gtg agt cag gaa cct gta ttg ttt gcc acc     1554
Arg Glu Ile Ile Gly Val Val Ser Gln Glu Pro Val Leu Phe Ala Thr
470             475                 480                 485 acg ata gct gaa aac att cgc tat ggt cgt gaa gat gtc acc atg gat     1602
Thr Ile Ala Glu Asn Ile Arg Tyr Gly Arg Glu Asp Val Thr Met Asp
            490                 495                 500 gag att gag aaa gct gtc aag gaa gcc aat gcc tat gac ttt atc atg     1650
Glu Ile Glu Lys Ala Val Lys Glu Ala Asn Ala Tyr Asp Phe Ile Met
            505                 510                 515 aaa ctg cct cag aaa ttt gac acc ctg gtt gga gag aga ggg gcc cag     1698
Lys Leu Pro Gln Lys Phe Asp Thr Leu Val Gly Glu Arg Gly Ala Gln
            520                 525                 530 ctg agt ggt ggg cag aag cag agg atc gcc att gca cgt gcc ctg gtt     1746
Leu Ser Gly Gly Gln Lys Gln Arg Ile Ala Ile Ala Arg Ala Leu Val
535                 540                 545 cgc aac ccc aag atc ctc ctg ctg gac gag gcc acg tca gcc ttg gac     1794
Arg Asn Pro Lys Ile Leu Leu Leu Asp Glu Ala Thr Ser Ala Leu Asp
550             555                 560                 565
```

```
aca gaa agt gaa gca gtg gtt cag gtg gct ctg gat aag gcc aga aaa      1842
Thr Glu Ser Glu Ala Val Val Gln Val Ala Leu Asp Lys Ala Arg Lys
            570                 575                 580 ggt cgg acc acc att gtg ata gct cat cgt ttg tct acg gtt cgt aat      1890
Gly Arg Thr Thr Ile Val Ile Ala His Arg Leu Ser Thr Val Arg Asn
        585                 590                 595 gcc gac gtc atc gct ggt ttc gat gat gga gtc att gtg gag aaa gga      1938
Ala Asp Val Ile Ala Gly Phe Asp Asp Gly Val Ile Val Glu Lys Gly
    600                 605                 610 aat cat gat gag ctc atg aaa gag aaa ggc att tac ttc aaa ctt gtc      1986
Asn His Asp Glu Leu Met Lys Glu Lys Gly Ile Tyr Phe Lys Leu Val
615                 620                 625 aca atg cag aca gca gga aat gaa att gaa tta gaa aat gca gct gat      2034
Thr Met Gln Thr Ala Gly Asn Glu Ile Glu Leu Glu Asn Ala Ala Asp
630                 635                 640                 645 gaa tcc aaa agt gaa att gat acc ttg gaa atg tct tca cat gat tca      2082
Glu Ser Lys Ser Glu Ile Asp Thr Leu Glu Met Ser Ser His Asp Ser
            650                 655                 660 gga tcc agt cta ata aga aaa aga tcc act cgt agg agt gtc cgt gga      2130
Gly Ser Ser Leu Ile Arg Lys Arg Ser Thr Arg Arg Ser Val Arg Gly
        665                 670                 675 tca caa ggc caa gac aga aag ctt agt acc aaa gag gct ctg gat gaa      2178
Ser Gln Gly Gln Asp Arg Lys Leu Ser Thr Lys Glu Ala Leu Asp Glu
    680                 685                 690 agt ata cct cca gtt tcc ttt tgg agg att atg aag cta aat tta act      2226
Ser Ile Pro Pro Val Ser Phe Trp Arg Ile Met Lys Leu Asn Leu Thr
695                 700                 705 gag tgg cct tat ttt gtt gtt ggt gta ttt tgt gcc att ata aat gga      2274
Glu Trp Pro Tyr Phe Val Val Gly Val Phe Cys Ala Ile Ile Asn Gly
710                 715                 720                 725 ggt ctg caa cca gca ttt gca gta ata ttt tca aag att ata ggg att      2322
Gly Leu Gln Pro Ala Phe Ala Val Ile Phe Ser Lys Ile Ile Gly Ile
            730                 735                 740 ttt aca aga aat gat gat gcc gaa aca aaa cga cag aat agt aac ttg      2370
Phe Thr Arg Asn Asp Asp Ala Glu Thr Lys Arg Gln Asn Ser Asn Leu
        745                 750                 755 ttt tca cta ttg ttt cta gtc ctt gga att gtt tct ttt att aca ttt      2418
Phe Ser Leu Leu Phe Leu Val Leu Gly Ile Val Ser Phe Ile Thr Phe
    760                 765                 770 ttc ctt cag ggc ttc aca ttt ggc aaa gct gga gag atc ctc acc aag      2466
Phe Leu Gln Gly Phe Thr Phe Gly Lys Ala Gly Glu Ile Leu Thr Lys
775                 780                 785 cgg ctc cga tac atg gtt ttc cga tcc atg ctc aga cag gat gtg agc      2514
Arg Leu Arg Tyr Met Val Phe Arg Ser Met Leu Arg Gln Asp Val Ser
790                 795                 800                 805 tgg ttt gat gac cct aaa aac acc act gga gca ttg act acc agg ctc      2562
Trp Phe Asp Asp Pro Lys Asn Thr Thr Gly Ala Leu Thr Thr Arg Leu
            810                 815                 820 gcc aat gat gct gct caa gtt aaa ggg gct ata ggt tcc agg ctt gct      2610
Ala Asn Asp Ala Ala Gln Val Lys Gly Ala Ile Gly Ser Arg Leu Ala
        825                 830                 835 ata att acc cag aat ata gca aat ctt ggg aca gga ata att ata tcc      2658
Ile Ile Thr Gln Asn Ile Ala Asn Leu Gly Thr Gly Ile Ile Ile Ser
    840                 845                 850 tta atc tat ggt tgg caa ctg aca ctg tta ctc tta gca att gta ccc      2706
Leu Ile Tyr Gly Trp Gln Leu Thr Leu Leu Leu Ala Ile Val Pro
855                 860                 865 atc att gca ata gca gga gtt gtt gaa atg aaa atg ttg tct gga caa      2754
Ile Ile Ala Ile Ala Gly Val Val Glu Met Lys Met Leu Ser Gly Gln
```

-continued

| | |
|---|---|
| 870 875 880 885 | |
| gca ctg aaa gat aag aaa gaa cta gaa ggt gct ggg aag atc gct act<br>Ala Leu Lys Asp Lys Lys Glu Leu Glu Gly Ala Gly Lys Ile Ala Thr<br>890 895 900 | 2802 |
| gaa gca ata gaa aac ttc cga act gtt gtt tct ttg act cag gag cag<br>Glu Ala Ile Glu Asn Phe Arg Thr Val Val Ser Leu Thr Gln Glu Gln<br>905 910 915 | 2850 |
| aag ttt gaa cat atg tat gat cag agt ttg cag gta cca tac aga aac<br>Lys Phe Glu His Met Tyr Asp Gln Ser Leu Gln Val Pro Tyr Arg Asn<br>920 925 930 | 2898 |
| tct ttg agg aaa gca cac atc ttt gga atc acg ttt tcc ttc acg cag<br>Ser Leu Arg Lys Ala His Ile Phe Gly Ile Thr Phe Ser Phe Thr Gln<br>935 940 945 | 2946 |
| gca atg atg tat ttt tcc tat gct gga tgt ttc cgg ttt gga gcc tac<br>Ala Met Met Tyr Phe Ser Tyr Ala Gly Cys Phe Arg Phe Gly Ala Tyr<br>950 955 960 965 | 2994 |
| ttg gtg gca cat agt ctc atg agc ttt gag gat gtt ctg tta gta ttt<br>Leu Val Ala His Ser Leu Met Ser Phe Glu Asp Val Leu Leu Val Phe<br>970 975 980 | 3042 |
| tca gct gtt gtc ttt ggt gcc atg gcc gtg ggg caa gtc agt tca ttt<br>Ser Ala Val Val Phe Gly Ala Met Ala Val Gly Gln Val Ser Ser Phe<br>985 990 995 | 3090 |
| gct cct gac tat gcc aaa gcc aaa gta tca gca gcc cac atc atc atg<br>Ala Pro Asp Tyr Ala Lys Ala Lys Val Ser Ala Ala His Ile Ile Met<br>1000 1005 1010 | 3138 |
| atc att gaa aaa acc cct ttg att gac agc tac agc aca gaa ggc cta<br>Ile Ile Glu Lys Thr Pro Leu Ile Asp Ser Tyr Ser Thr Glu Gly Leu<br>1015 1020 1025 | 3186 |
| aag ccg aac aca ttg gaa gga aat gtc aca ttt aat gaa gtt gta ttc<br>Lys Pro Asn Thr Leu Glu Gly Asn Val Thr Phe Asn Glu Val Val Phe<br>1030 1035 1040 1045 | 3234 |
| aac tat ccc acc cga ctg gac atc cca gtg ctt cag ggg ctg agc ctg<br>Asn Tyr Pro Thr Arg Leu Asp Ile Pro Val Leu Gln Gly Leu Ser Leu<br>1050 1055 1060 | 3282 |
| gaa gtg aag aag ggc cag acg ctg gcc ctg gtg ggc agc agt ggc tgt<br>Glu Val Lys Lys Gly Gln Thr Leu Ala Leu Val Gly Ser Ser Gly Cys<br>1065 1070 1075 | 3330 |
| ggg aag agc acg gtg gtc cag ctc ctg gag cgg ttc tat gac ccc ttg<br>Gly Lys Ser Thr Val Val Gln Leu Leu Glu Arg Phe Tyr Asp Pro Leu<br>1080 1085 1090 | 3378 |
| gcg ggg aaa gtg ctg ctt gac ggc aaa gaa ata aag caa ctg aat gtt<br>Ala Gly Lys Val Leu Leu Asp Gly Lys Glu Ile Lys Gln Leu Asn Val<br>1095 1100 1105 | 3426 |
| cag tgg ctc cga gca cac ctg ggc atc gtg tcc cag gag ccc atc ctg<br>Gln Trp Leu Arg Ala His Leu Gly Ile Val Ser Gln Glu Pro Ile Leu<br>1110 1115 1120 1125 | 3474 |
| ttt gac tgc agc att agt gag aac att gcc tat gga gac aac agc cgg<br>Phe Asp Cys Ser Ile Ser Glu Asn Ile Ala Tyr Gly Asp Asn Ser Arg<br>1130 1135 1140 | 3522 |
| gtg gtg tca cag gaa gag atc gtg agg gca gcc aag gag gcc aat ata<br>Val Val Ser Gln Glu Glu Ile Val Arg Ala Ala Lys Glu Ala Asn Ile<br>1145 1150 1155 | 3570 |
| cac gcc ttc atc gag tca ctg cct aat aaa tat agc acc aga gta gga<br>His Ala Phe Ile Glu Ser Leu Pro Asn Lys Tyr Ser Thr Arg Val Gly<br>1160 1165 1170 | 3618 |
| gac aaa gga act cag ctc tct ggt ggc cag aaa caa cgc att gcc ata<br>Asp Lys Gly Thr Gln Leu Ser Gly Gly Gln Lys Gln Arg Ile Ala Ile<br>1175 1180 1185 | 3666 |
| gct cgt gcc ctt gtt aga cag cct cat att ttg ctt ttg gat gaa gcc | 3714 |

```
Ala Arg Ala Leu Val Arg Gln Pro His Ile Leu Leu Leu Asp Glu Ala
1190                1195                1200                1205 aca tca gct ctg gat aca gaa agt gaa aag gtt gtc caa gaa gcc ctg      3762
Thr Ser Ala Leu Asp Thr Glu Ser Glu Lys Val Val Gln Glu Ala Leu
            1210                1215                1220 gac aaa gcc aga gaa ggc cgt acc tgc att gtg att gct cac cgc ctg      3810
Asp Lys Ala Arg Glu Gly Arg Thr Cys Ile Val Ile Ala His Arg Leu
        1225                1230                1235 tcc acc atc cag aat gca gac tta ata gtg gtg ttt cag aat ggc aga      3858
Ser Thr Ile Gln Asn Ala Asp Leu Ile Val Val Phe Gln Asn Gly Arg
    1240                1245                1250 gtc aag gag cac ggc aca cat cag cag ctg ctg gca cag aaa ggc atc      3906
Val Lys Glu His Gly Thr His Gln Gln Leu Leu Ala Gln Lys Gly Ile
1255                1260                1265 tat ttt tca atg gtc agt gtc cag gct gga gca aag cgc cag t            3949
Tyr Phe Ser Met Val Ser Val Gln Ala Gly Ala Lys Arg Gln
1270                1275                1280 gaactgtgac tgtatgagat gttaaatatt ttttaatatt tgtgtttaaa tatggcattt   4009
attcaaagtt aaaaagcaag tacttataga attatgaaga gttatctgtt taacatttcc   4069
tcaaccaagt tcagagtctt cagacactcg taattaaagg aagagagcga gagacatcat   4129
caagtggaga gaaataatgg tttaaattgc attataaatt ttataacaga gttaaagtag   4189
attttt                                                               4195

<210> SEQ ID NO 4
<211> LENGTH: 1283
<212> TYPE: PRT
<213> ORGANISM: Macaca fascicularis

<400> SEQUENCE: 4

Met Asp Leu Glu Gly Asp Arg Asn Gly Gly Ala Glu Lys Lys Asn Phe
1               5                   10                  15

Phe Lys Leu Asn Asn Lys Ser Lys Lys Asp Lys Lys Glu Arg Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Asp Met Thr Asp Thr Phe Ala
65                  70                  75                  80

Asn Ala Gly Asn Leu Gly Asp Leu Gly Ala Leu Leu Phe Asn Asn Thr
                85                  90                  95

Asn Ser Ser Asn Ile Thr Asp Thr Val Pro Val Met Asn Leu Glu Glu
            100                 105                 110

Asp Met Thr Arg Tyr Ala Tyr Tyr Tyr Ser Gly Ile Gly Ala Gly Val
        115                 120                 125

Leu Val Ala Ala Tyr Ile Gln Val Ser Phe Trp Cys Leu Ala Ala Gly
    130                 135                 140

Arg Gln Ile His Lys Ile Arg Lys Gln Phe Phe His Ala Ile Met Arg
145                 150                 155                 160

Gln Glu Ile Gly Trp Phe Asp Val His Asp Val Gly Glu Leu Asn Thr
                165                 170                 175

Arg Leu Thr Asp Asp Val Ser Lys Ile Asn Glu Gly Ile Gly Asp Lys
            180                 185                 190

Ile Gly Met Phe Phe Gln Ser Met Ala Thr Phe Phe Thr Gly Phe Ile
        195                 200                 205
```

```
Val Gly Phe Thr Arg Gly Trp Lys Leu Thr Leu Val Ile Leu Ala Ile
    210                 215                 220

Ser Pro Val Leu Gly Leu Ser Ala Ala Val Trp Ala Lys Ile Leu Ser
225                 230                 235                 240

Ser Phe Thr Asp Lys Glu Leu Leu Ala Tyr Ala Lys Ala Gly Ala Val
                245                 250                 255

Ala Glu Glu Val Leu Ala Ala Ile Arg Thr Val Ile Ala Phe Gly Gly
            260                 265                 270

Gln Lys Lys Glu Leu Glu Arg Tyr Asn Lys Asn Leu Glu Glu Ala Lys
        275                 280                 285

Arg Ile Gly Ile Lys Lys Ala Ile Thr Ala Asn Ile Ser Ile Gly Ala
    290                 295                 300

Ala Phe Leu Leu Ile Tyr Ala Ser Tyr Ala Leu Ala Phe Trp Tyr Gly
305                 310                 315                 320

Thr Thr Leu Val Leu Ser Lys Glu Tyr Ser Ile Gly Gln Val Leu Thr
                325                 330                 335

Val Phe Phe Ser Val Leu Ile Gly Ala Phe Ser Val Gly Gln Ala Ser
            340                 345                 350

Pro Ser Ile Glu Ala Phe Ala Asn Ala Arg Gly Ala Ala Phe Glu Ile
        355                 360                 365

Phe Lys Ile Ile Asp Asn Lys Pro Ser Ile Asp Ser Tyr Ser Lys Ser
    370                 375                 380

Gly His Lys Pro Asp Asn Ile Lys Gly Asn Leu Glu Phe Arg Asn Val
385                 390                 395                 400

His Phe Ser Tyr Pro Ser Arg Lys Glu Val Lys Ile Leu Lys Gly Leu
                405                 410                 415

Asn Leu Lys Val Gln Ser Gly Gln Thr Val Ala Leu Val Gly Asn Ser
            420                 425                 430

Gly Cys Gly Lys Ser Thr Thr Val Gln Leu Met Gln Arg Leu Tyr Asp
        435                 440                 445

Pro Thr Glu Gly Met Val Ser Val Asp Gly Gln Asp Ile Arg Thr Ile
    450                 455                 460

Asn Val Arg Phe Leu Arg Glu Ile Ile Gly Val Val Ser Gln Glu Pro
465                 470                 475                 480

Val Leu Phe Ala Thr Thr Ile Ala Glu Asn Ile Arg Tyr Gly Arg Glu
                485                 490                 495

Asp Val Thr Met Asp Glu Ile Glu Lys Ala Val Lys Glu Ala Asn Ala
            500                 505                 510

Tyr Asp Phe Ile Met Lys Leu Pro Gln Lys Phe Asp Thr Leu Val Gly
        515                 520                 525

Glu Arg Gly Ala Gln Leu Ser Gly Gly Gln Lys Gln Arg Ile Ala Ile
    530                 535                 540

Ala Arg Ala Leu Val Arg Asn Pro Lys Ile Leu Leu Leu Asp Glu Ala
545                 550                 555                 560

Thr Ser Ala Leu Asp Thr Glu Ser Glu Ala Val Val Gln Val Ala Leu
                565                 570                 575

Asp Lys Ala Arg Lys Gly Arg Thr Thr Ile Val Ile Ala His Arg Leu
            580                 585                 590

Ser Thr Val Arg Asn Ala Asp Val Ile Ala Gly Phe Asp Asp Gly Val
        595                 600                 605

Ile Val Glu Lys Gly Asn His Asp Glu Leu Met Lys Glu Lys Gly Ile
    610                 615                 620
```

-continued

Tyr Phe Lys Leu Val Thr Met Gln Thr Ala Gly Asn Glu Ile Glu Leu
625                 630                 635                 640

Glu Asn Ala Ala Asp Glu Ser Lys Ser Glu Ile Asp Thr Leu Glu Met
            645                 650                 655

Ser Ser His Asp Ser Gly Ser Ser Leu Ile Arg Lys Arg Ser Thr Arg
                660                 665                 670

Arg Ser Val Arg Gly Ser Gln Gly Gln Asp Arg Lys Leu Ser Thr Lys
            675                 680                 685

Glu Ala Leu Asp Glu Ser Ile Pro Pro Val Ser Phe Trp Arg Ile Met
690                 695                 700

Lys Leu Asn Leu Thr Glu Trp Pro Tyr Phe Val Val Gly Val Phe Cys
705                 710                 715                 720

Ala Ile Ile Asn Gly Gly Leu Gln Pro Ala Phe Ala Val Ile Phe Ser
                725                 730                 735

Lys Ile Ile Gly Ile Phe Thr Arg Asn Asp Asp Ala Glu Thr Lys Arg
                740                 745                 750

Gln Asn Ser Asn Leu Phe Ser Leu Leu Phe Leu Val Leu Gly Ile Val
            755                 760                 765

Ser Phe Ile Thr Phe Phe Leu Gln Gly Phe Thr Phe Gly Lys Ala Gly
770                 775                 780

Glu Ile Leu Thr Lys Arg Leu Arg Tyr Met Val Phe Arg Ser Met Leu
785                 790                 795                 800

Arg Gln Asp Val Ser Trp Phe Asp Asp Pro Lys Asn Thr Thr Gly Ala
                805                 810                 815

Leu Thr Thr Arg Leu Ala Asn Asp Ala Ala Gln Val Lys Gly Ala Ile
            820                 825                 830

Gly Ser Arg Leu Ala Ile Ile Thr Gln Asn Ile Ala Asn Leu Gly Thr
            835                 840                 845

Gly Ile Ile Ile Ser Leu Ile Tyr Gly Trp Gln Leu Thr Leu Leu Leu
            850                 855                 860

Leu Ala Ile Val Pro Ile Ile Ala Ile Ala Gly Val Val Glu Met Lys
865                 870                 875                 880

Met Leu Ser Gly Gln Ala Leu Lys Asp Lys Lys Glu Leu Glu Gly Ala
                885                 890                 895

Gly Lys Ile Ala Thr Glu Ala Ile Glu Asn Phe Arg Thr Val Val Ser
                900                 905                 910

Leu Thr Gln Glu Gln Lys Phe Glu His Met Tyr Asp Gln Ser Leu Gln
            915                 920                 925

Val Pro Tyr Arg Asn Ser Leu Arg Lys Ala His Ile Phe Gly Ile Thr
            930                 935                 940

Phe Ser Phe Thr Gln Ala Met Met Tyr Phe Ser Tyr Ala Gly Cys Phe
945                 950                 955                 960

Arg Phe Gly Ala Tyr Leu Val Ala His Ser Leu Met Ser Phe Glu Asp
                965                 970                 975

Val Leu Leu Val Phe Ser Ala Val Phe Gly Ala Met Ala Val Gly
            980                 985                 990

Gln Val Ser Ser Phe Ala Pro Asp Tyr Ala Lys Ala Lys Val Ser Ala
            995                 1000                1005

Ala His Ile Ile Met Ile Ile Glu Lys Thr Pro Leu Ile Asp Ser Tyr
        1010                1015                1020

Ser Thr Glu Gly Leu Lys Pro Asn Thr Leu Glu Gly Asn Val Thr Phe
1025                1030                1035                1040

Asn Glu Val Val Phe Asn Tyr Pro Thr Arg Leu Asp Ile Pro Val Leu

```
                   1045                1050                1055
Gln Gly Leu Ser Leu Glu Val Lys Lys Gly Gln Thr Leu Ala Leu Val
                1060                1065                1070

Gly Ser Ser Gly Cys Gly Lys Ser Thr Val Val Gln Leu Leu Glu Arg
            1075                1080                1085

Phe Tyr Asp Pro Leu Ala Gly Lys Val Leu Leu Asp Gly Lys Glu Ile
        1090                1095                1100

Lys Gln Leu Asn Val Gln Trp Leu Arg Ala His Leu Gly Ile Val Ser
1105                1110                1115                1120

Gln Glu Pro Ile Leu Phe Asp Cys Ser Ile Ser Glu Asn Ile Ala Tyr
                1125                1130                1135

Gly Asp Asn Ser Arg Val Val Ser Gln Glu Glu Ile Val Arg Ala Ala
                1140                1145                1150

Lys Glu Ala Asn Ile His Ala Phe Ile Glu Ser Leu Pro Asn Lys Tyr
                1155                1160                1165

Ser Thr Arg Val Gly Asp Lys Gly Thr Gln Leu Ser Gly Gly Gln Lys
            1170                1175                1180

Gln Arg Ile Ala Ile Ala Arg Ala Leu Val Arg Gln Pro His Ile Leu
1185                1190                1195                1200

Leu Leu Asp Glu Ala Thr Ser Ala Leu Asp Thr Glu Ser Glu Lys Val
                1205                1210                1215

Val Gln Glu Ala Leu Asp Lys Ala Arg Glu Gly Arg Thr Cys Ile Val
                1220                1225                1230

Ile Ala His Arg Leu Ser Thr Ile Gln Asn Ala Asp Leu Ile Val Val
            1235                1240                1245

Phe Gln Asn Gly Arg Val Lys Glu His Gly Thr His Gln Gln Leu Leu
        1250                1255                1260

Ala Gln Lys Gly Ile Tyr Phe Ser Met Val Ser Val Gln Ala Gly Ala
1265                1270                1275                1280

Lys Arg Gln

<210> SEQ ID NO 5
<211> LENGTH: 1280
<212> TYPE: PRT
<213> ORGANISM: Homo sapiens

<400> SEQUENCE: 5

Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
```

-continued

```
            130                 135                 140
His Lys Ile Arg Lys Gln Phe Phe His Ala Ile Met Arg Gln Glu Ile
145                 150                 155                 160
Gly Trp Phe Asp Val His Asp Val Gly Glu Leu Asn Thr Arg Leu Thr
                    165                 170                 175
Asp Asp Val Ser Lys Ile Asn Glu Val Ile Gly Asp Lys Ile Gly Met
                180                 185                 190
Phe Phe Gln Ser Met Ala Thr Phe Thr Gly Phe Ile Val Gly Phe
            195                 200                 205
Thr Arg Gly Trp Lys Leu Thr Leu Val Ile Leu Ala Ile Ser Pro Val
        210                 215                 220
Leu Gly Leu Ser Ala Ala Val Trp Ala Lys Ile Leu Ser Ser Phe Thr
225                 230                 235                 240
Asp Lys Glu Leu Leu Ala Tyr Ala Lys Ala Gly Ala Val Ala Glu Glu
                245                 250                 255
Val Leu Ala Ala Ile Arg Thr Val Ile Ala Phe Gly Gly Gln Lys Lys
                260                 265                 270
Glu Leu Glu Arg Tyr Asn Lys Asn Leu Glu Glu Ala Lys Arg Ile Gly
            275                 280                 285
Ile Lys Lys Ala Ile Thr Ala Asn Ile Ser Ile Gly Ala Ala Phe Leu
        290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Phe
                325                 330                 335
Ser Val Leu Ile Gly Ala Phe Ser Val Gly Gln Ala Ser Pro Ser Ile
                340                 345                 350
Glu Ala Phe Ala Asn Ala Arg Gly Ala Ala Tyr Glu Ile Phe Lys Ile
            355                 360                 365
Ile Asp Asn Lys Pro Ser Ile Asp Ser Tyr Ser Lys Ser Gly His Lys
        370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                405                 410                 415
Val Gln Ser Gly Gln Thr Val Ala Leu Val Gly Asn Ser Gly Cys Gly
                420                 425                 430
Lys Ser Thr Thr Val Gln Leu Met Gln Arg Leu Tyr Asp Pro Thr Glu
            435                 440                 445
Gly Met Val Ser Val Asp Gly Gln Asp Ile Arg Thr Ile Asn Val Arg
        450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
                500                 505                 510
Ile Met Lys Leu Pro His Lys Phe Asp Thr Leu Val Gly Glu Arg Gly
            515                 520                 525
Ala Gln Leu Ser Gly Gly Gln Lys Gln Arg Ile Ala Ile Ala Arg Ala
        530                 535                 540
Leu Val Arg Asn Pro Lys Ile Leu Leu Leu Asp Glu Ala Thr Ser Ala
545                 550                 555                 560
```

```
Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
                690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
                770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
                850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
                930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975
```

-continued

```
Val Phe Ser Ala Val Phe Gly Ala Met Ala Val Gly Gln Val Ser
            980             985             990
Ser Phe Ala Pro Asp Tyr Ala Lys Ala Lys Ile Ser Ala Ala His Ile
            995             1000            1005
Ile Met Ile Ile Glu Lys Thr Pro Leu Ile Asp Ser Tyr Ser Thr Glu
    1010            1015            1020
Gly Leu Met Pro Asn Thr Leu Glu Gly Asn Val Thr Phe Gly Glu Val
1025            1030            1035            1040
Val Phe Asn Tyr Pro Thr Arg Pro Asp Ile Pro Val Leu Gln Gly Leu
                1045            1050            1055
Ser Leu Glu Val Lys Lys Gly Gln Thr Leu Ala Leu Val Gly Ser Ser
                1060            1065            1070
Gly Cys Gly Lys Ser Thr Val Val Gln Leu Leu Glu Arg Phe Tyr Asp
                1075            1080            1085
Pro Leu Ala Gly Lys Val Leu Leu Asp Gly Lys Glu Ile Lys Arg Leu
                1090            1095            1100
Asn Val Gln Trp Leu Arg Ala His Leu Gly Ile Val Ser Gln Glu Pro
1105            1110            1115            1120
Ile Leu Phe Asp Cys Ser Ile Ala Glu Asn Ile Ala Tyr Gly Asp Asn
                1125            1130            1135
Ser Arg Val Val Ser Gln Glu Glu Ile Val Arg Ala Ala Lys Glu Ala
                1140            1145            1150
Asn Ile His Ala Phe Ile Glu Ser Leu Pro Asn Lys Tyr Ser Thr Lys
                1155            1160            1165
Val Gly Asp Lys Gly Thr Gln Leu Ser Gly Gly Gln Lys Gln Arg Ile
                1170            1175            1180
Ala Ile Ala Arg Ala Leu Val Arg Gln Pro His Ile Leu Leu Leu Asp
1185            1190            1195            1200
Glu Ala Thr Ser Ala Leu Asp Thr Glu Ser Glu Lys Val Val Gln Glu
                1205            1210            1215
Ala Leu Asp Lys Ala Arg Glu Gly Arg Thr Cys Ile Val Ile Ala His
                1220            1225            1230
Arg Leu Ser Thr Ile Gln Asn Ala Asp Leu Ile Val Val Phe Gln Asn
                1235            1240            1245
Gly Arg Val Lys Glu His Gly Thr His Gln Gln Leu Leu Ala Gln Lys
                1250            1255            1260
Gly Ile Tyr Phe Ser Met Val Ser Val Gln Ala Gly Thr Lys Arg Gln
1265            1270            1275            1280
```

<210> SEQ ID NO 6
<211> LENGTH: 1279
<212> TYPE: PRT
<213> ORGANISM: Homo sapiens

<400> SEQUENCE: 6

```
Met Asp Leu Glu Gly Asp Arg Asn Gly Gly Ala Lys Lys Lys Asn Phe
1               5               10              15
Phe Lys Leu Asn Asn Lys Ser Glu Lys Asp Lys Lys Glu Lys Lys Pro
                20              25              30
Thr Val Ser Val Phe Ser Met Phe Arg Tyr Ser Asn Trp Leu Asp Lys
            35              40              45
Leu Tyr Met Val Val Gly Thr Leu Ala Ala Ile Ile His Gly Ala Gly
        50              55              60
Leu Pro Leu Met Met Leu Val Phe Gly Glu Met Thr Asp Ile Phe Ala
65              70              75              80
```

```
Asn Ala Gly Asn Leu Glu Asp Leu Met Ser Asn Ile Thr Asn Arg Ser
                85                  90                  95
Asp Ile Asn Asp Thr Gly Phe Phe Met Asn Leu Glu Glu Asp Met Thr
            100                 105                 110
Arg Tyr Ala Tyr Tyr Tyr Ser Gly Ile Gly Ala Gly Val Leu Val Ala
            115                 120                 125
Ala Tyr Ile Gln Val Ser Phe Trp Cys Leu Ala Ala Gly Arg Gln Ile
            130                 135                 140
His Lys Ile Arg Lys Gln Phe Phe His Ala Ile Met Arg Gln Glu Ile
145                 150                 155                 160
Gly Trp Phe Asp Val His Asp Val Gly Glu Leu Asn Thr Arg Leu Thr
                165                 170                 175
Asp Asp Val Ser Lys Ile Asn Glu Gly Ile Gly Asp Lys Ile Gly Met
                180                 185                 190
Phe Phe Gln Ser Met Ala Thr Phe Phe Thr Gly Phe Ile Val Gly Phe
                195                 200                 205
Thr Arg Gly Trp Lys Leu Thr Leu Val Ile Leu Ala Ile Ser Pro Val
            210                 215                 220
Leu Gly Leu Ser Ala Ala Val Trp Ala Lys Ile Leu Ser Ser Phe Thr
225                 230                 235                 240
Asp Lys Glu Leu Leu Ala Tyr Ala Lys Ala Gly Ala Val Ala Glu Glu
                245                 250                 255
Val Leu Ala Ala Ile Arg Thr Val Ile Ala Phe Gly Gly Gln Lys Lys
                260                 265                 270
Glu Leu Glu Arg Tyr Asn Lys Asn Leu Glu Glu Ala Lys Arg Ile Gly
            275                 280                 285
Ile Lys Lys Ala Ile Thr Ala Asn Ile Ser Ile Gly Ala Ala Phe Leu
            290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Ser
                325                 330                 335
Val Leu Ile Gly Ala Phe Ser Val Gly Gln Ala Ser Pro Ser Ile Glu
                340                 345                 350
Ala Phe Ala Asn Ala Arg Gly Ala Ala Tyr Glu Ile Phe Lys Ile Ile
            355                 360                 365
Asp Asn Lys Pro Ser Ile Asp Ser Tyr Ser Lys Ser Gly His Lys Pro
            370                 375                 380
Asp Asn Ile Lys Gly Asn Leu Glu Phe Arg Asn Val His Phe Ser Tyr
385                 390                 395                 400
Pro Ser Arg Lys Glu Val Lys Ile Leu Lys Gly Leu Asn Leu Lys Val
                405                 410                 415
Gln Ser Gly Gln Thr Val Ala Leu Val Gly Asn Ser Gly Cys Gly Lys
                420                 425                 430
Ser Thr Thr Val Gln Leu Met Gln Arg Leu Tyr Asp Pro Thr Glu Gly
            435                 440                 445
Met Val Ser Val Asp Gly Gln Asp Ile Arg Thr Ile Asn Val Arg Phe
450                 455                 460
Leu Arg Glu Ile Ile Gly Val Val Ser Gln Glu Pro Val Leu Phe Ala
465                 470                 475                 480
Thr Thr Ile Ala Glu Asn Ile Arg Tyr Gly Arg Glu Asn Val Thr Met
                485                 490                 495
```

-continued

```
Asp Glu Ile Glu Lys Ala Val Lys Glu Ala Asn Ala Tyr Asp Phe Ile
            500                 505                 510
Met Lys Leu Pro His Lys Phe Asp Thr Leu Val Gly Glu Arg Gly Ala
        515                 520                 525
Gln Leu Ser Gly Gly Gln Lys Gln Arg Ile Ala Ile Ala Arg Ala Leu
    530                 535                 540
Val Arg Asn Pro Lys Ile Leu Leu Leu Asp Glu Ala Thr Ser Ala Leu
545                 550                 555                 560
Asp Thr Glu Ser Glu Ala Val Val Gln Val Ala Leu Asp Lys Ala Arg
                565                 570                 575
Lys Gly Arg Thr Thr Ile Val Ile Ala His Arg Leu Ser Thr Val Arg
            580                 585                 590
Asn Ala Asp Val Ile Ala Gly Phe Asp Asp Gly Val Ile Val Glu Lys
        595                 600                 605
Gly Asn His Asp Glu Leu Met Lys Glu Lys Gly Ile Tyr Phe Lys Leu
    610                 615                 620
Val Thr Met Gln Thr Ala Gly Asn Glu Val Glu Leu Glu Asn Ala Ala
625                 630                 635                 640
Asp Glu Ser Lys Ser Glu Ile Asp Ala Leu Glu Met Ser Ser Asn Asp
                645                 650                 655
Ser Arg Ser Ser Leu Ile Arg Lys Arg Ser Thr Arg Arg Ser Val Arg
            660                 665                 670
Gly Ser Gln Ala Gln Asp Arg Lys Leu Ser Thr Lys Glu Ala Leu Asp
        675                 680                 685
Glu Ser Ile Pro Pro Val Ser Phe Trp Arg Ile Met Lys Leu Asn Leu
    690                 695                 700
Thr Glu Trp Pro Tyr Phe Val Val Gly Val Phe Cys Ala Ile Ile Asn
705                 710                 715                 720
Gly Gly Leu Gln Pro Ala Phe Ala Ile Ile Phe Ser Lys Ile Ile Gly
                725                 730                 735
Val Phe Thr Arg Ile Asp Asp Pro Glu Thr Lys Arg Gln Asn Ser Asn
            740                 745                 750
Leu Phe Ser Leu Leu Phe Leu Ala Leu Gly Ile Ile Ser Phe Ile Thr
        755                 760                 765
Phe Phe Leu Gln Gly Phe Thr Phe Gly Lys Ala Gly Glu Ile Leu Thr
    770                 775                 780
Lys Arg Leu Arg Tyr Met Val Phe Arg Ser Met Leu Arg Gln Asp Val
785                 790                 795                 800
Ser Trp Phe Asp Asp Pro Lys Asn Thr Thr Gly Ala Leu Thr Thr Arg
                805                 810                 815
Leu Ala Asn Asp Ala Ala Gln Val Lys Gly Ala Ile Gly Ser Arg Leu
            820                 825                 830
Ala Val Ile Thr Gln Asn Ile Ala Asn Leu Gly Thr Gly Ile Ile Ile
        835                 840                 845
Ser Phe Ile Tyr Gly Trp Gln Leu Thr Leu Leu Leu Leu Ala Ile Val
    850                 855                 860
Pro Ile Ile Ala Ile Ala Gly Val Val Glu Met Lys Met Leu Ser Gly
865                 870                 875                 880
Gln Ala Leu Lys Asp Lys Lys Glu Leu Glu Gly Ala Gly Lys Ile Ala
                885                 890                 895
Thr Glu Ala Ile Glu Asn Phe Arg Thr Val Val Ser Leu Thr Gln Glu
            900                 905                 910
Gln Lys Phe Glu His Met Tyr Ala Gln Ser Leu Gln Val Pro Tyr Arg
```

```
                    915                 920                 925
Asn Ser Leu Arg Lys Ala His Ile Phe Gly Ile Thr Phe Ser Phe Thr
                930                 935                 940
Gln Ala Met Met Tyr Phe Ser Tyr Ala Gly Cys Phe Arg Phe Gly Ala
945                 950                 955                 960
Tyr Leu Val Ala His Lys Leu Met Ser Phe Glu Asp Val Leu Leu Val
                965                 970                 975
Phe Ser Ala Val Val Phe Gly Ala Met Ala Val Gly Gln Val Ser Ser
                980                 985                 990
Phe Ala Pro Asp Tyr Ala Lys Ala Lys Ile Ser Ala Ala His Ile Ile
                995                 1000                1005
Met Ile Ile Glu Lys Thr Pro Leu Ile Asp Ser Tyr Ser Thr Glu Gly
                1010                1015                1020
Leu Met Pro Asn Thr Leu Glu Gly Asn Val Thr Phe Gly Glu Val Val
1025                1030                1035                1040
Phe Asn Tyr Pro Thr Arg Pro Asp Ile Pro Val Leu Gln Gly Leu Ser
                1045                1050                1055
Leu Glu Val Lys Lys Gly Gln Thr Leu Ala Leu Val Gly Ser Ser Gly
                1060                1065                1070
Cys Gly Lys Ser Thr Val Val Gln Leu Leu Glu Arg Phe Tyr Asp Pro
                1075                1080                1085
Leu Ala Gly Lys Val Leu Leu Asp Gly Lys Glu Ile Lys Arg Leu Asn
                1090                1095                1100
Val Gln Trp Leu Arg Ala His Leu Gly Ile Val Ser Gln Glu Pro Ile
1105                1110                1115                1120
Leu Phe Asp Cys Ser Ile Ala Glu Asn Ile Ala Tyr Gly Asp Asn Ser
                1125                1130                1135
Arg Val Val Ser Gln Glu Glu Ile Val Arg Ala Ala Lys Glu Ala Asn
                1140                1145                1150
Ile His Ala Phe Ile Glu Ser Leu Pro Asn Lys Tyr Ser Thr Lys Val
                1155                1160                1165
Gly Asp Lys Gly Thr Gln Leu Ser Gly Gly Gln Lys Gln Arg Ile Ala
                1170                1175                1180
Ile Ala Arg Ala Leu Val Arg Gln Pro His Ile Leu Leu Leu Asp Glu
1185                1190                1195                1200
Ala Thr Ser Ala Leu Asp Thr Glu Ser Glu Lys Val Val Gln Glu Ala
                1205                1210                1215
Leu Asp Lys Ala Arg Glu Gly Arg Thr Cys Ile Val Ile Ala His Arg
                1220                1225                1230
Leu Ser Thr Ile Gln Asn Ala Asp Leu Ile Val Val Phe Gln Asn Gly
                1235                1240                1245
Arg Val Lys Glu His Gly Thr His Gln Gln Leu Leu Ala Gln Lys Gly
                1250                1255                1260
Ile Tyr Phe Ser Met Val Ser Val Gln Ala Gly Thr Lys Arg Gln
1265                1270                1275

<210> SEQ ID NO 7
<211> LENGTH: 1280
<212> TYPE: PRT
<213> ORGANISM: Canis familiaris

<400> SEQUENCE: 7

Met Asp Pro Glu Gly Gly Arg Lys Gly Ser Ala Glu Lys Asn Phe Trp
1               5                   10                  15
```

-continued

```
Lys Met Gly Lys Lys Ser Lys Lys Glu Lys Lys Glu Lys Lys Pro Thr
        20                  25                  30
Val Ser Thr Phe Ala Met Phe Arg Tyr Ser Asn Trp Leu Asp Arg Leu
            35                  40                  45
Tyr Met Leu Val Gly Thr Met Ala Ala Ile Ile His Gly Ala Ala Leu
    50                  55                  60
Pro Leu Met Met Leu Val Phe Gly Asn Met Thr Asp Ser Phe Ala Asn
65                  70                  75                  80
Ala Gly Ile Ser Arg Asn Lys Thr Phe Pro Val Ile Ile Asn Glu Ser
                85                  90                  95
Ile Thr Asn Asn Thr Gln His Phe Ile Asn His Leu Glu Glu Glu Met
                100                 105                 110
Thr Thr Tyr Ala Tyr Tyr Ser Gly Ile Gly Ala Gly Val Leu Val
            115                 120                 125
Ala Ala Tyr Ile Gln Val Ser Phe Trp Cys Leu Ala Ala Gly Arg Gln
        130                 135                 140
Ile Leu Lys Ile Arg Lys Gln Phe Phe His Ala Ile Met Arg Gln Glu
145                 150                 155                 160
Ile Gly Trp Phe Asp Val His Asp Val Gly Glu Leu Asn Thr Arg Leu
                165                 170                 175
Thr Asp Asp Val Ser Lys Ile Asn Glu Gly Ile Gly Asp Lys Val Gly
            180                 185                 190
Met Phe Phe Gln Ser Ile Ala Thr Phe Phe Thr Gly Phe Ile Val Gly
        195                 200                 205
Phe Thr Pro Gly Trp Lys Leu Thr Leu Val Ile Leu Ala Ile Ser Pro
    210                 215                 220
Val Leu Gly Leu Ser Ala Ala Ile Trp Ala Lys Ile Leu Ser Ser Phe
225                 230                 235                 240
Thr Asp Lys Glu Leu Leu Ala Tyr Ala Lys Ala Gly Ala Val Ala Glu
                245                 250                 255
Glu Val Leu Ala Ala Ile Arg Thr Val Ile Ala Phe Gly Gly Gln Lys
            260                 265                 270
Lys Glu Leu Glu Arg Tyr Asn Lys Asn Leu Glu Glu Ala Lys Arg Ile
        275                 280                 285
Gly Ile Lys Lys Ala Ile Thr Ala Asn Ile Ser Ile Gly Ala Ala Phe
        290                 295                 300
Leu Leu Ile Tyr Ala Ser Tyr Ala Leu Ala Phe Trp Tyr Gly Thr Ser
305                 310                 315                 320
Leu Val Leu Ser Ser Glu Tyr Thr Ile Gly Gln Val Leu Thr Val Phe
                325                 330                 335
Phe Ser Val Leu Ile Gly Ala Phe Ser Ile Gly Gln Ala Ser Pro Ser
            340                 345                 350
Ile Glu Ala Phe Ala Asn Ala Arg Gly Ala Ala Tyr Glu Ile Phe Lys
        355                 360                 365
Ile Ile Asp Asn Lys Pro Ser Ile Asp Ser Tyr Ser Lys Ser Gly His
    370                 375                 380
Lys Pro Asp Asn Ile Lys Gly Asn Leu Glu Phe Lys Asn Val His Phe
385                 390                 395                 400
Ser Tyr Pro Ser Arg Lys Glu Val Lys Ile Leu Lys Gly Leu Asn Leu
                405                 410                 415
Lys Val Gln Ser Gly Gln Thr Val Ala Leu Val Gly Asn Ser Gly Cys
            420                 425                 430
Gly Lys Ser Thr Thr Val Gln Leu Met Gln Arg Leu Tyr Asp Pro Thr
```

-continued

```
                435                 440                 445
Asp Gly Met Val Cys Ile Asp Gly Gln Asp Ile Arg Thr Ile Asn Val
            450                 455                 460
Arg His Leu Arg Glu Ile Thr Gly Val Val Ser Gln Glu Pro Val Leu
465                 470                 475                 480
Phe Ala Thr Thr Ile Ala Glu Asn Ile Arg Tyr Gly Arg Glu Asn Val
                485                 490                 495
Thr Met Asp Glu Ile Glu Lys Ala Val Lys Glu Ala Asn Ala Tyr Asp
            500                 505                 510
Phe Ile Met Lys Leu Pro Asn Lys Phe Asp Thr Leu Val Gly Glu Arg
                515                 520                 525
Gly Ala Arg Leu Ser Gly Gly Gln Lys Gln Arg Ile Ala Ile Ala Arg
            530                 535                 540
Ala Leu Val Arg Asn Pro Lys Ile Leu Leu Leu Asp Glu Ala Thr Ser
545                 550                 555                 560
Ala Leu Asp Thr Glu Ser Glu Ala Val Val Gln Val Ala Leu Asp Lys
                565                 570                 575
Ala Arg Lys Gly Arg Thr Thr Ile Val Ile Ala His Arg Leu Ser Thr
            580                 585                 590
Val Arg Asn Ala Asp Val Ile Ala Gly Phe Asp Asp Gly Val Ile Val
                595                 600                 605
Glu Lys Gly Asn His Asp Glu Leu Met Lys Glu Lys Gly Ile Tyr Phe
            610                 615                 620
Lys Leu Val Thr Met Gln Thr Arg Gly Asn Glu Ile Glu Leu Glu Asn
625                 630                 635                 640
Ala Thr Gly Glu Ser Lys Ser Glu Ser Asp Ala Leu Glu Met Ser Pro
                645                 650                 655
Lys Asp Ser Gly Ser Ser Leu Ile Lys Arg Arg Ser Thr Arg Arg Ser
            660                 665                 670
Ile His Ala Pro Gln Gly Gln Asp Arg Lys Leu Gly Thr Lys Glu Asp
                675                 680                 685
Leu Asn Glu Asn Val Pro Ser Val Ser Phe Trp Arg Ile Leu Lys Leu
            690                 695                 700
Asn Ser Thr Glu Trp Pro Tyr Phe Val Val Gly Ile Phe Cys Ala Ile
705                 710                 715                 720
Ile Asn Gly Gly Leu Gln Pro Ala Phe Ser Ile Ile Phe Ser Arg Ile
                725                 730                 735
Ile Gly Ile Phe Thr Arg Asp Glu Asp Pro Glu Thr Lys Arg Gln Asn
            740                 745                 750
Ser Asn Met Phe Ser Val Leu Phe Leu Val Leu Gly Ile Ile Ser Phe
            755                 760                 765
Ile Thr Phe Phe Leu Gln Gly Phe Thr Phe Gly Lys Ala Gly Glu Ile
            770                 775                 780
Leu Thr Lys Arg Leu Arg Tyr Met Val Phe Arg Ser Met Leu Arg Gln
785                 790                 795                 800
Asp Val Ser Trp Phe Asp Asp Pro Lys Asn Thr Thr Gly Ala Leu Thr
                805                 810                 815
Thr Arg Leu Ala Asn Asp Ala Ala Gln Val Lys Gly Ala Ile Gly Ser
            820                 825                 830
Arg Leu Ala Val Ile Thr Gln Asn Ile Ala Asn Leu Gly Thr Gly Ile
            835                 840                 845
Ile Ile Ser Leu Ile Tyr Gly Trp Gln Leu Thr Leu Leu Leu Leu Ala
            850                 855                 860
```

```
Ile Val Pro Ile Ile Ala Ile Ala Gly Val Val Glu Met Lys Met Leu
865                 870                 875                 880

Ser Gly Gln Ala Leu Lys Asp Lys Lys Glu Leu Glu Gly Ala Gly Lys
                885                 890                 895

Ile Ala Thr Glu Ala Ile Glu Asn Phe Arg Thr Val Val Ser Leu Thr
                900                 905                 910

Arg Glu Gln Lys Phe Glu Tyr Met Tyr Ala Gln Ser Leu Gln Val Pro
                915                 920                 925

Tyr Arg Asn Ser Leu Arg Lys Ala His Ile Phe Gly Val Ser Phe Ser
        930                 935                 940

Ile Thr Gln Ala Met Met Tyr Phe Ser Tyr Ala Gly Cys Phe Arg Phe
945                 950                 955                 960

Gly Ala Tyr Leu Val Ala Asn Glu Phe Met Asn Phe Gln Asp Val Leu
                965                 970                 975

Leu Val Phe Ser Ala Ile Val Phe Gly Ala Met Ala Val Gly Gln Val
                980                 985                 990

Ser Ser Phe Ala Pro Asp Tyr Ala Lys Ala Lys Val Ser Ala Ala His
        995                 1000                1005

Val Ile Met Ile Ile Glu Lys Ser Pro Leu Ile Asp Ser Tyr Ser Pro
    1010                1015                1020

His Gly Leu Lys Pro Asn Thr Leu Glu Gly Asn Val Thr Phe Asn Glu
1025                1030                1035                1040

Val Val Phe Asn Tyr Pro Thr Arg Pro Asp Ile Pro Val Leu Gln Gly
                1045                1050                1055

Leu Ser Leu Glu Val Lys Lys Gly Gln Thr Leu Ala Leu Val Gly Ser
                1060                1065                1070

Ser Gly Cys Gly Lys Ser Thr Val Val Gln Leu Leu Glu Arg Phe Tyr
        1075                1080                1085

Asp Pro Leu Ala Gly Ser Val Leu Ile Asp Gly Lys Glu Ile Lys His
            1090                1095                1100

Leu Asn Val Gln Trp Leu Arg Ala His Leu Gly Ile Val Ser Gln Glu
1105                1110                1115                1120

Pro Ile Leu Phe Asp Cys Ser Ile Ala Glu Asn Ile Ala Tyr Gly Asp
            1125                1130                1135

Asn Ser Arg Val Val Ser His Glu Glu Ile Met Gln Ala Ala Lys Glu
        1140                1145                1150

Ala Asn Ile His His Phe Ile Glu Thr Leu Pro Glu Lys Tyr Asn Thr
        1155                1160                1165

Arg Val Gly Asp Lys Gly Thr Gln Leu Ser Gly Gly Gln Lys Gln Arg
    1170                1175                1180

Ile Ala Ile Ala Arg Ala Leu Val Arg Gln Pro His Ile Leu Leu Leu
1185                1190                1195                1200

Asp Glu Ala Thr Ser Ala Leu Asp Thr Glu Ser Glu Lys Val Val Gln
                1205                1210                1215

Glu Ala Leu Asp Lys Ala Arg Glu Gly Arg Thr Cys Ile Val Ile Ala
            1220                1225                1230

His Arg Leu Ser Thr Ile Gln Asn Ala Asp Leu Ile Val Val Phe Gln
        1235                1240                1245

Asn Gly Lys Val Lys Glu His Gly Thr His Gln Gln Leu Leu Ala Gln
    1250                1255                1260

Lys Gly Ile Tyr Phe Ser Met Ile Ser Val Gln Ala Gly Ala Lys Arg
1265                1270                1275                1280
```

```
<210> SEQ ID NO 8
<211> LENGTH: 368
<212> TYPE: PRT
<213> ORGANISM: Canis familiaris

<400> SEQUENCE: 8

Thr Ser Ala Leu Asp Thr Glu Ser Glu Ala Val Val Gln Val Ala Leu
 1               5                   10                  15

Asp Lys Ala Arg Lys Gly Arg Thr Thr Ile Val Ile Ala His Arg Leu
            20                  25                  30

Ser Thr Val Arg Asn Ala Asp Val Ile Ala Gly Phe Asp Asp Gly Val
        35                  40                  45

Ile Val Glu Lys Gly Asn His Asp Glu Leu Met Lys Glu Lys Gly Ile
50                  55                  60

Tyr Phe Lys Leu Val Thr Met Gln Thr Arg Gly Asn Glu Ile Asp Leu
65                  70                  75                  80

Glu Asn Ala Thr Gly Glu Ser Lys Ser Glu Ser Asp Ala Leu Glu Met
                85                  90                  95

Ser Pro Lys Asp Ser Gly Ser Ser Leu Ile Lys Arg Arg Ser Thr Arg
            100                 105                 110

Arg Ser Ile His Ala Pro Gln Gly Gln Asp Arg Lys Leu Gly Thr Lys
        115                 120                 125

Glu Asp Leu Asn Glu Asn Val Pro Pro Val Ser Phe Trp Arg Ile Leu
130                 135                 140

Lys Leu Asn Ser Thr Glu Trp Pro Tyr Phe Val Val Gly Ile Phe Cys
145                 150                 155                 160

Ala Ile Ile Asn Gly Gly Leu Gln Pro Ala Phe Ser Ile Ile Phe Ser
                165                 170                 175

Arg Ile Ile Gly Ile Phe Thr Arg Asp Glu Asp Pro Glu Thr Lys Arg
            180                 185                 190

Gln Ile Ser Asn Met Phe Ser Val Leu Phe Leu Val Leu Gly Ile Ile
        195                 200                 205

Ser Phe Ile Thr Phe Phe Leu Gln Gly Phe Thr Phe Gly Lys Ala Gly
210                 215                 220

Glu Ile Leu Thr Lys Arg Leu Arg Tyr Met Val Phe Arg Ser Met Leu
225                 230                 235                 240

Arg Gln Asp Val Ser Trp Phe Asp Asp Leu Lys Asn Thr Thr Gly Ala
                245                 250                 255

Leu Thr Thr Arg Leu Ala Asn Asp Ala Ala Gln Val Lys Gly Ala Ile
            260                 265                 270

Gly Ser Arg Leu Ala Val Ile Thr Gln Asn Ile Ala Asn Leu Gly Thr
        275                 280                 285

Gly Ile Ile Ile Ser Leu Ile Tyr Gly Trp Gln Leu Thr Leu Leu Leu
290                 295                 300

Leu Ala Ile Val Pro Ile Ile Ala Ile Ala Gly Val Val Glu Met Lys
305                 310                 315                 320

Met Leu Ser Gly Gln Ala Leu Lys Asp Lys Lys Glu Leu Glu Gly Ala
                325                 330                 335

Gly Lys Ile Ala Thr Glu Ala Ile Glu Asn Phe Arg Thr Val Val Ser
            340                 345                 350

Leu Thr Gln Glu Gln Lys Phe Glu His Met Tyr Ala Gln Ser Leu Gln
        355                 360                 365

<210> SEQ ID NO 9
```

-continued

```
<211> LENGTH: 27
<212> TYPE: DNA
<213> ORGANISM: Homo sapiens

<400> SEQUENCE: 9
ctggacttcc tctcatgatg ctggtgt                                27

<210> SEQ ID NO 10
<211> LENGTH: 28
<212> TYPE: DNA
<213> ORGANISM: Homo sapiens

<400> SEQUENCE: 10
gacagctatt cgaagagtgg gcacaaac                               28

<210> SEQ ID NO 11
<211> LENGTH: 24
<212> TYPE: DNA
<213> ORGANISM: Homo sapiens

<400> SEQUENCE: 11
ggccatggca ccaaagacaa cagc                                   24

<210> SEQ ID NO 12
<211> LENGTH: 23
<212> TYPE: DNA
<213> ORGANISM: Macaca fascicularis

<400> SEQUENCE: 12
ttggacacag aaagtgaagc agt                                    23

<210> SEQ ID NO 13
<211> LENGTH: 20
<212> TYPE: DNA
<213> ORGANISM: Macaca fascicularis

<400> SEQUENCE: 13
ctgagcatgg atcggaaaac                                        20

<210> SEQ ID NO 14
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 14
ttgtaatacg actcactata gggcgaat                               28

<210> SEQ ID NO 15
<211> LENGTH: 28
<212> TYPE: DNA
<213> ORGANISM: Artificial Sequence
<220> FEATURE:
<223> OTHER INFORMATION: Synthetic oligonucleotide based on Macaca
      fascicularis and Homo sapiens

<400> SEQUENCE: 15
cttttcgaga tgggtaactg aagtgaac                               28

<210> SEQ ID NO 16
<211> LENGTH: 28
<212> TYPE: DNA
<213> ORGANISM: Artificial Sequence
<220> FEATURE:
```

-continued

```
<223> OTHER INFORMATION: Synthetic oligonucleotide based on Macaca
      fascicularis and Homo sapiens

<400> SEQUENCE: 16
agaaggtgct gggaagatcg ctactgaa                                      28

<210> SEQ ID NO 17
<211> LENGTH: 18
<212> TYPE: DNA
<213> ORGANISM: Macaca fascicularis

<400> SEQUENCE: 17
gcctaaagcc gaacacat                                                 18

<210> SEQ ID NO 18
<211> LENGTH: 21
<212> TYPE: DNA
<213> ORGANISM: Macaca fascicularis

<400> SEQUENCE: 18
ctattaagtc tgcattctgg a                                             21
```